US006536219B2

(12) United States Patent
Peters

(10) Patent No.: US 6,536,219 B2
(45) Date of Patent: Mar. 25, 2003

(54) APPARATUS AND METHOD FOR PRECISION CRYOEMBEDDING OF TISSUE SAMPLES

(76) Inventor: Steven Peters, 410 Old Mill La., Wycoff, NJ (US) 07481

( * ) Notice: Subject to any disclaimer, the term of this patent is extended or adjusted under 35 U.S.C. 154(b) by 20 days.

(21) Appl. No.: 09/848,152

(22) Filed: May 3, 2001

(65) Prior Publication Data

US 2002/0162337 A1 Nov. 7, 2002

(51) Int. Cl.⁷ .................. F25D 25/00; F25C 5/02; F25C 5/14; B01L 11/00; G01N 1/00
(52) U.S. Cl. .............. 62/62; 62/320; 62/341; 165/80.1; 422/104; 436/174
(58) Field of Search ............ 62/62, 3.2, 51.1, 62/293, 320, 341, 383; 165/80.1; 422/63, 104, 101; 436/174

(56) References Cited

U.S. PATENT DOCUMENTS

| | | | | |
|---|---|---|---|---|
| 3,218,896 A | * | 11/1965 | McCormick | 83/15 |
| 3,319,289 A | * | 5/1967 | McCormick | 425/117 |
| 3,639,999 A | * | 2/1972 | Adams | 34/92 |
| 3,982,862 A | * | 9/1976 | Pickett et al. | 425/117 |
| 4,557,903 A | * | 12/1985 | McCormick | 422/101 |
| 4,623,308 A | * | 11/1986 | Hellon | 425/117 |
| 4,695,339 A | | 9/1987 | Rada | 156/80 |
| 4,752,347 A | | 6/1988 | Rada | 156/382 |
| 5,257,128 A | * | 10/1993 | Diller et al. | 359/395 |
| 5,628,197 A | | 5/1997 | Rada | 62/62 |
| 5,776,298 A | * | 7/1998 | Franks | 156/390 |
| 5,837,198 A | * | 11/1998 | Itani | 422/63 |
| 5,983,991 A | * | 11/1999 | Franks | 165/80.1 |
| 6,017,476 A | * | 1/2000 | Renshaw | 264/158 |
| 6,094,923 A | | 8/2000 | Rada | 62/51.1 |
| 6,199,623 B1 | * | 3/2001 | Franks | 165/80.1 |

* cited by examiner

Primary Examiner—William C. Doerrler
(74) Attorney, Agent, or Firm—Eugene C. Rzucidlo

(57) ABSTRACT

An apparatus for quick freezing tissue specimens has the advantage of precise predictable embedding orientation. The apparatus includes embedding wells, chucks and over-chuck cooling blocks. Additional components include a cooled cutting board, freezing plate griddle and elevated freezing block. Tools created to use with the system include a dislodging bar, a spatula/pry tool, a dispensing slide and a flattening tool. The combination of these elements function at −25 to −30 degrees C. to precisely prepare tissue specimens for frozen sectioning. The apparatus can be cooled and adapted by several methods: (1) as a stand-alone bench top cryoembedding station refrigerated by compressor and Peltier devices: (2) as modular portable units cooled in a separate refrigeration device such as a cryostat or freezer; and (3) built into cryostat work chambers as part of the internal embedding center.

50 Claims, 30 Drawing Sheets

Chucks

Crossing channels allow excess embedding medium to extrude. Flat surface of prepared block.

APPARATUS AND METHOD FOR PRECISION CRYOEMBEDDING OF TISSUE SAMPLES

FIELD OF THE INVENTION

This invention is directed to the apparatus and techniques used in the preparation of tissue for microscopic analysis using the technique of frozen sectioning. The invention offers rapid and superior quality preparation while saving time, reducing tissue wastage and improving precision to augment the pathologists ability to diagnose the most difficult tissue samples.

BACKGROUND OF THE INVENTION

In many commonly performed surgical procedures, pathologists or other trained medical professionals are called upon to render rapid interpretation of tissue samples so that the surgeon can make a decision on how to proceed with the operation. The pathologist may be asked to diagnose a disease such as a tumor or an infection or to aid in evaluating the extent of a disease. Commonly, in tumor processes, he is asked to determine involvement of resection margins to answer the question of whether the surgeon has completely removed all of the diseased tissue or still needs to remove more. In order for the pathologist to provide this rapid interpretation, he must use a technique known as frozen sectioning. In many cases, the information needed by the surgeon demands a degree of precision which is difficult or impossible to provide due to the limitations of the available techniques of embedding and freezing.

Frozen sectioning refers to the ultra-thin slicing of tissue to a thickness that is usually about 5–7 mm using an instrument called a cryostat. A cryostat is a refrigerated device, which cools a cutting instrument, known as a cryotome, so that frozen tissues can be cut at the desired thickness. Tissue prepared for microscopic examination by pathologists (and other scientists and technologists) must be hardened to a degree where it can be cut extremely thin. In routine tissue preparation this is accomplished by a time consuming process of fixation, dehydration, solvent infiltration, paraffin infiltration, embedding in blocks of paraffin following which the sample can be cut, stained and interpreted under the microscope. This process takes hours at the minimum and is not suitable for quick, intraoperative interpretation, which needs to be accomplished in a period of minutes, so that the surgeon can make the therapeutic decisions on how to proceed with the surgery.

A faster method of hardening a tissue sample for rapid cutting and preparation of slides is the technique of frozen sectioning. This technique involves hardening the tissue sample by freezing and cutting it on the cryotome, after which a sample can be stained and read. This process can be performed in less than 10 minutes.

The preparation of tissue (freezing and embedding, i.e. cryoembedding) prior to sectioning (cutting on the cryotome) can be performed in several ways. In one method, a cryostat is typically fitted with an area for freezing a chuck (specimen holder). This can be a simple bar or surface on which to sit a flat bottomed chuck or a hole in the surface in which to place the stem of a chuck having a stem. The typical process involves placing a quantity of mounting medium on the chuck and then placing the tissue face up on the medium. The chuck is set upon the cold freezing surface and is cooled from the underside. Often, a flattening cold weight, sometimes referred to as a heat extractor, is placed on top of the specimen to flatten the surface and aid in freezing the sample. The resulting specimen surface is not parallel to the chuck and varies from preparation to preparation. The face of the prepared sample then requires considerable trimming using the cryotome until the desired section is available. This method functions adequately in large samples where tissue wastage is inconsequential and where precision is not critical. However, this method can be difficult or impossible to apply accurately to minute, irregular, flimsy, rubbery and liquefied specimens without undesirable tissue loss or uninterpretable results.

Other methods of preparing tissue include immersing a face up chuck with applied tissue into liquid nitrogen or a dry ice slurry for rapid freezing. Although rapid freezing is possible, precise orientation remains a drawback. Attempts at instrumentation resulting in face-down embedding, a surface flattening process that uses various freezing devices, have improved some aspects of the process yet still do not afford the level of precision necessary to answer all of the surgeons inquiries.

These conventional frozen section preparation techniques are limited in the ability to precisely embed and orient tissue samples. When performed inside the cryostat the process is cumbersome, unpredictable and often results in a block face which is slanted with respect to the tissue face showing portions of the specimen, with other important areas buried in the frozen embedding medium. The block requires significant tissue trimming and wastage in order to approximate the desired section. Often the desired section cannot be achieved because one side has been trimmed away before the more important aspect has been reached. The problem is analogous to trying to uncover an object buried at an angle in the ground. One needs to go much deeper to uncover the deeper side of the object. In the case of a frozen tissue block, considerable attrition occurs when tissue is trimmed away "digging" for the desired area. Another problem with current methodologies is the difficulty of freezing small or difficult to handle specimens embedded at the proper position in the frozen medium (the process known as embedding) so that the tissue face to be cut will be precisely oriented to yield the desired view on the microscopic slide. As a result, the pathologist is unable to answer the question asked of him.

An additional drawback to current methodologies is that the embedding procedures are often performed while the pathologist is bent over and stretching to do meticulous work inside the deep box-like chamber of the cryostat, a situation not conducive to fine motor tasks or the urgency of the frozen section process. The importance of the questions being asked of the pathologist is of the highest medical importance, as inaccurate results have severe potential for morbidity or mortality. Examples include deciding if a malignant tumor such as a breast or colon cancer has been completely removed where a discrepant result could lead to recurrence, metastasis or death, or deciding if a small skin tumor of the eyelid is completely removed where a discrepant result could lead to recurrence and potential loss of the eye. Such examples are an everyday occurrence in the practice of the pathologist.

SUMMARY OF THE INVENTION

The present invention is an apparatus and methodology to provide rapid, precise tissue specimen preparation for use in the frozen section process. This invention prepares multiple specimens at a time with simple preparation, minimal monitoring and results in a highly precise preparation while greatly reducing tissue wastage and affording a level of accuracy that is unprecedented. The apparatus can be applied as a stand-alone instrument, modular units or built into existing or new cryostat designs.

It is an object of the system and method of the present invention to provide a highly precise, rapid preparation of frozen section specimen blocks in a ergonomically comfortable work space so the pathologist can maximize his manual and diagnostic skills to answer any and all questions demanded of him. The features of this apparatus and method accomplish this objective. This apparatus is in its most sophisticated form a cryoembedding station that provides an easy access bench top work area allowing the pathologist complete use of manual skills. The instrument rapidly freezes multiple samples at the same time with a minimum of preparation time and needs no monitoring of the freezing process once the wells are filled. The process of face down embedding on the adherent surface results in flat, predictably and reliably oriented specimen faces that are parallel to the chuck face. This results in greatly reduced trimming and wastage of tissue, and reduces the need for readjustment of the specimen holder angle. The lack of tissue compression by the weighted heat extractor eliminates compression artifacts and slanted surfaces and buried tissue. The blocks that are created are surrounded by an ample "handle" of embedding medium resulting in considerable ease in the cutting by frozen sectioning process. The square wells yield blocks with straight sides which reduce tendency to roll when parallel to the blade and provide a easy to manipulate long handle when cut diagonal to the blade. The large wells can yield large flat panoramic sections or can allow for multiple samples. These large samples can be cut with little trimming and wastage due to the flat parallel block faces. The result is that a considerably larger amount of tissue can be prepared with each single preparation, decreasing the number of blocks that need to be cut. This saves time for the pathologist and surgeon and cost for the patient.

This invention also includes and facilitates an original technique, referred to as "Frozen Block Cryoembedding", which affords a level of precision and accuracy of orientation and embedding previously impossible by conventional methods. The technique allows precise preparation of: (1) minute specimens; (2) thin flat and tubular specimens; (3) torn perforated or friable specimens; (4) flimsy soft specimens difficult to cut with a scalpel; and (5) flattening and orientation of curling, rubbery, angular or curved tissues. The versatility of the apparatus described herein affords a myriad of applications to solve problems in precision embedding and is limited only by the imagination of the pathologists.

BRIEF DESCRIPTION OF THE DRAWINGS

FIG. 21a depicts the minute skin sample.

FIG. 21b depicts the inked sample.

FIG. 21c depicts the sample on the floor of the well filled with embedding medium.

FIG. 21d depicts the flat side of the freezing block over the well surface.

FIG. 21e depicts the sample frozen in a block of embedding medium (lines scored to show path of scalpel).

FIG. 21f depicts the frozen block slices face up for demonstration.

FIG. 21g depicts the slices face down in the embedding well.

FIG. 21h depicts the completed embedded frozen sample.

FIG. 22a depicts the perforated skin sample.

FIG. 22b depicts the sample after freezing in a block of embedding medium (lines scored to show path of scalpel.)

FIG. 22c depicts the sliced specimen turned on its side.

FIG. 22d depicts the completed embedded frozen sample.

FIG. 28a depicts a worm approximately 1.5 mm diameter.

FIG. 28b depicts the worm after freezing in a block of embedding medium and slicing.

FIG. 28c depicts the prepared completed frozen specimen after trimming.

FIG. 28d depicts a stained microscopic view of 28c showing a perfect cross section of this difficult to handle specimen.

FIG. 29a depicts a rubbery folded portion of colonic tissue.

FIG. 29b depicts the tissue adhering to the freezing plate and being stretched and flattened as it adheres to the freezing plate.

FIG. 29c depicts the tissue frozen in a block of embedding medium.

FIG. 29d depicts the sliced colonic tissue, easily turned on its side, demonstrating a perfect cross section of all layers of the colon wall.

DETAILED DESCRIPTION OF THE INVENTION

A first aspect of the invention is an apparatus for rapidly freezing and precisely embedding tissues for frozen sections at below freezing temperatures, preferably in the range of about −25 to −30 degrees C. The apparatus of the invention includes a platform, block or bar with a flat polished surface, collectively referred to herein as a platform, one or more embedding wells milled into the surface, one or more sample holders, referred to herein as chucks, sized to fit over the embedding wells, and one or more cooling blocks sized to fit over the chucks. In a preferred embodiment, the platform, the chucks and the cooling blocks are made of stainless steel. The apparatus also includes a freezing plate, a cutting board, an elevated freezing block, a dislodging tool, a prying tool, a dispensing slide, and a tissue flattening tool. These components are described in detail below.

Figure 3:
FIG. 3 depicts two exemplary embedding wells.

The embedding wells are intended to receive tissue samples that are to be cryoembedded. A well is milled into the surface of the platform. Its floor is parallel to the platform surface. The well is polished, and can come in varying sizes, shapes and depths. Although circular and rectangular shaped wells are the most common, the shape of the well is unimportant to the invention. Wells are spaced at specific intervals on the platform surface to accommodate chucks. Wells can also be notched for use in the frozen block cryoembedding preparation, described below. The walls of the well are beveled to form an angle that is greater than 90 degrees with respect to the base. The beveling is needed to enable the samples to be easily removed from the wells without damaging the preparation. A preferred range for the beveling angle is from about 95 to about 135 degrees, although the angle can be any greater angle less than 180 degrees. The inventor has found that a beveling angle of about 105 degrees works well. Wells are polished on all surfaces. The outer lip of the well is rounded and polished. The platform surface is also polished. Polishing the platform surface and well enables easy release of the frozen specimen block. FIG. 3 depicts a notched square well along with an unnotched well.

In one preferred embodiment for use in pathology, typical well sizes can range from 5 mm wide at the base up to 50 mm wide at the base, with depths ranging from 3 to 4 mm. Rectangular wells can have rounded corners with a typical radius of 4–5 mm. The wells are slightly larger at the top edge due to the beveling of the well walls. The size of an embedding well is determined by the type of samples it is intended to receive. Embedding wells used to prepare samples for research can be much bigger. For example, a researcher wishing to section an entire heart would need a well big enough to embed the heart. A well can optionally include a notch carved at the center of one side which over its length falls from the level of the surface of the block or bar to the floor of the well. These notched wells serve a duel function in block preparation for frozen block cryoembedding.

Figure 4:
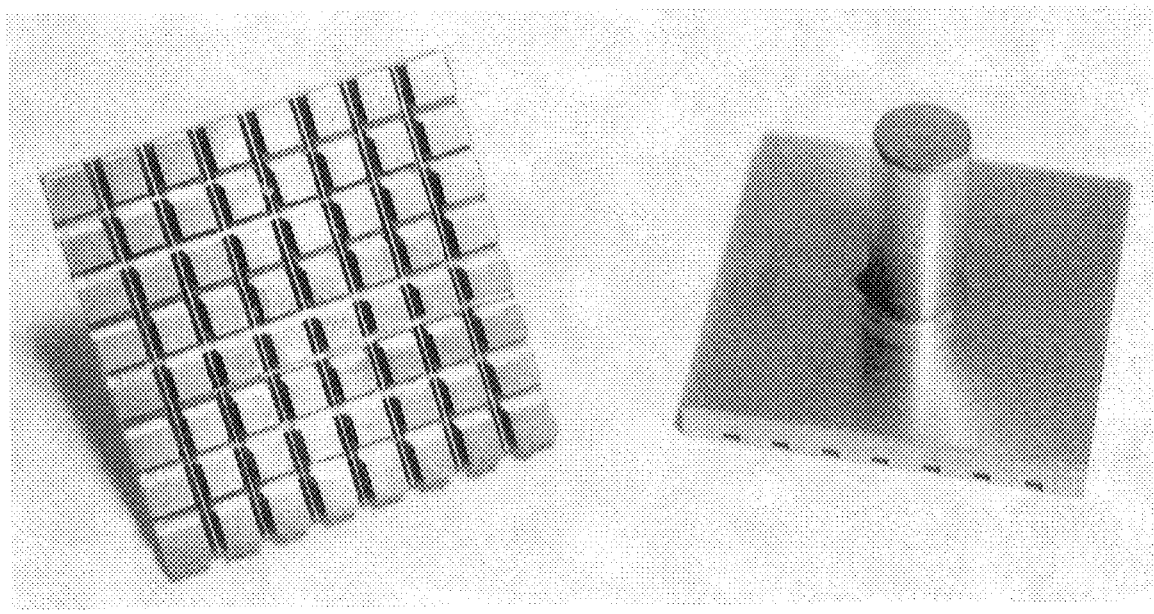
FIG. 4 depicts two views of a sample holder or chuck.

The cryostat chucks, preferably made of stainless steel, are to be applied flush to the surface of the steel block over the embedding wells. The chucks are designed with a face having a grid of sharply cut channels that afford a degree of adhesive strength to the specimen while at the same time allowing extrusion of excess embedding medium. This results in a flat sample surface parallel to the face of the chuck. Chucks can be either stemmed or stemless. In a preferred embodiment, the thickness of the chuck face is much less than its width. Although a chuck with a thicker face can initially cool a sample quite effectively by itself, once warmed it cannot be quickly re-cooled to working temperature, reducing its cooling ability. The inventor found that thin-faced chucks, when used with the cooling blocks described next, performed better. The thickness, material and surface area of a chuck are chosen to optimize cold retention for maximum freezing power when used cold while still able, when used with a cooling block, to extract heat from the filled well to the cooling block when used warm. FIG. 4 depicts the channeled face and stem of a typical square chuck.

Figure 5:
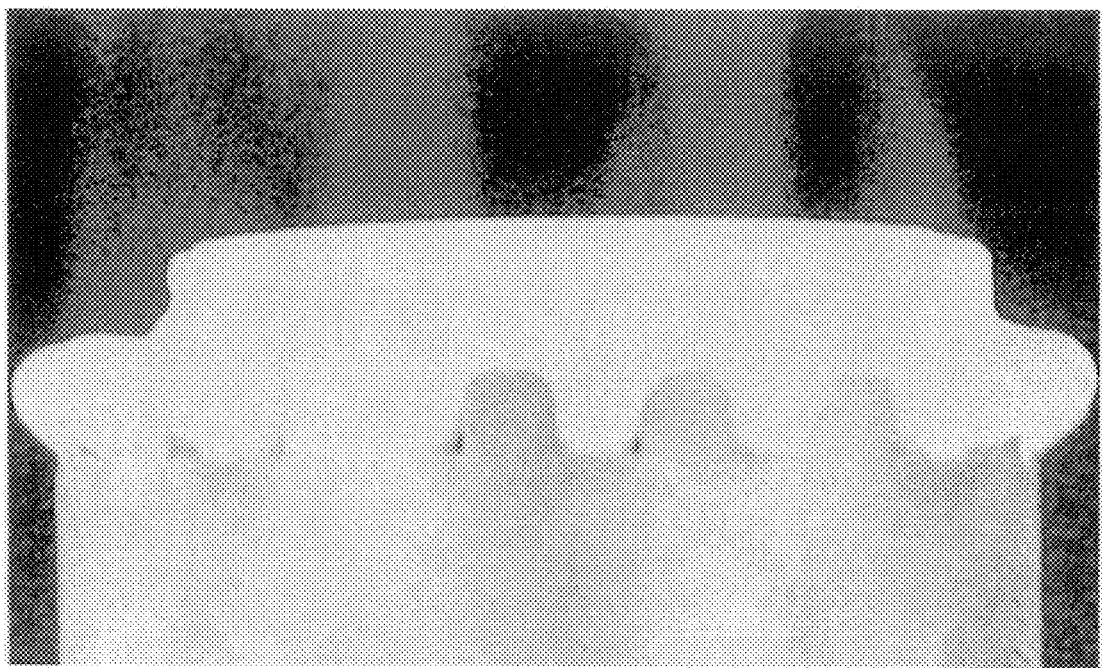
FIG. 5 depicts the extrusion of embedding medium from a chuck and the flat surface as viewed from the side.
Figure 19:
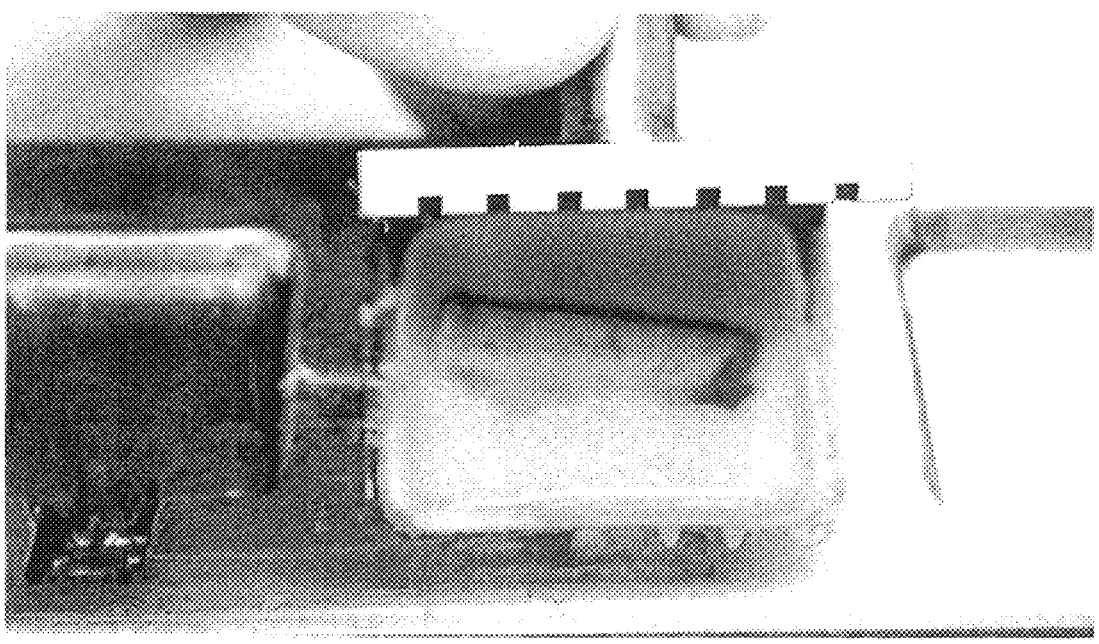
FIG. 19 depicts a well filled with embedding medium, with a chuck placed over a well.
Figure 20:
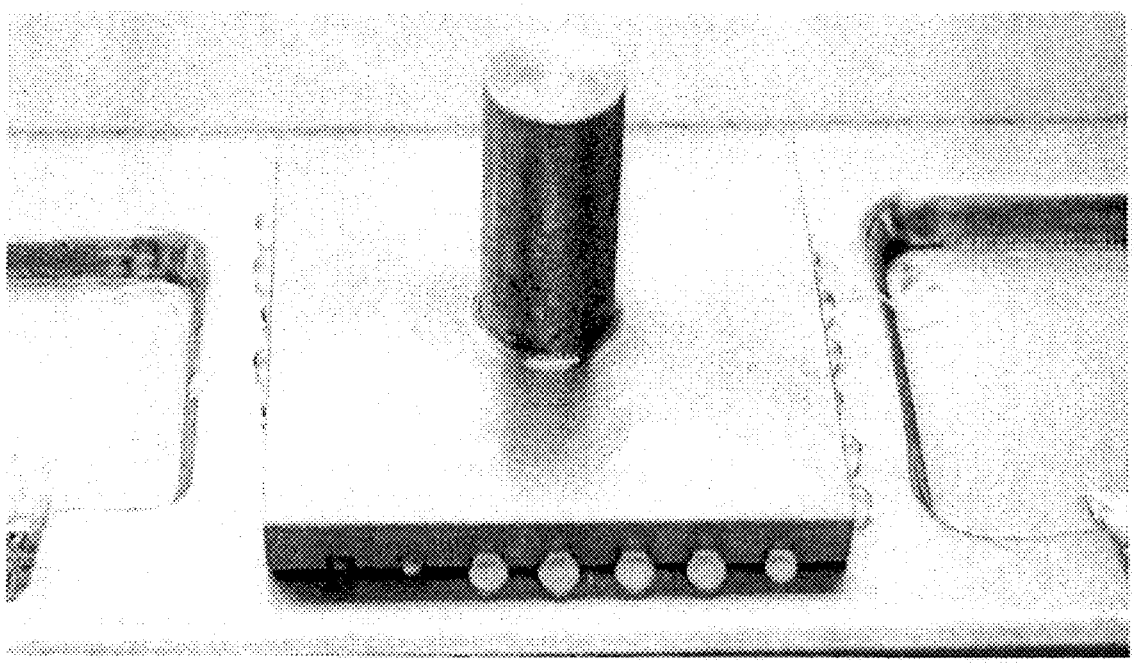
FIG. 20 depicts the chuck covering the well.

In one preferred embodiment, chucks have a face thickness of about 4.0 mm. The face can be either square or circular and is big enough to cover an embedding well without falling in. The face has two groups of channels cut the length of the face at right angles to each other. The chuck depicted in FIG. 4 measures 36 mm on a side, and the channels are 1.5×1.5 mm square spaced at 3 mm intervals. The inventor has found that square cross-sectioned channels work best for balancing adherence of the sample to the chuck while maximizing the shearing strength of the bond between the sample and the chuck. Attached to the base of the chuck, opposite of the channeled face is a stem or some other attachment means specifically designed to fit cooling blocks fitted for stemless chucks. The stem in the chuck shown in FIG. 4 measures 9×20 mm. The meniscus of the embedding medium bulges above the top of the well, as can be seen in FIG. 19, and thus when the chuck face is pressed on the meniscus the crossed grid of channels fill with embedding medium creating a gripping surface to tightly hold the freezing medium, as illustrated in FIGS. 5 and 20. The crossing channel design allows extrusion of excess medium at the edge of the chuck face so the chuck can be pressed flat and flush to the surface face of the steel platform or block into which wells are milled. This results in a flat specimen face parallel to the chuck face.

Figure 6:
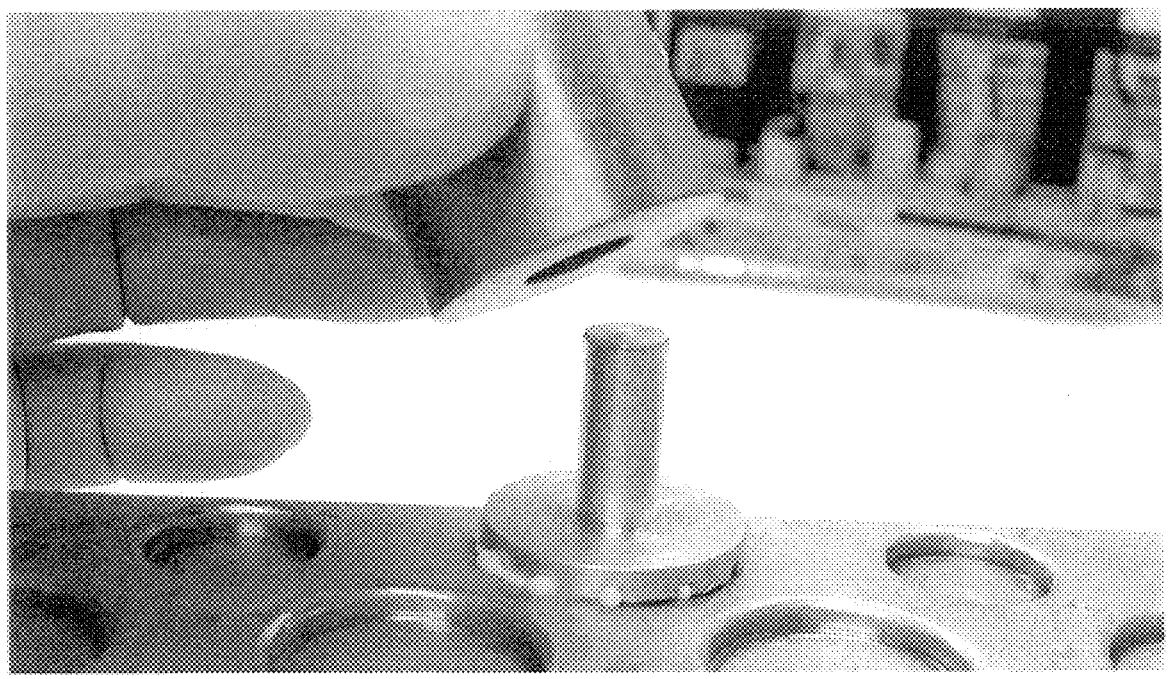
FIG. 6 depicts an overchuck cooling block being placed over a chuck.

An over chuck cooling block is used to extract heat from the chuck, and is sized to fit over a chuck. A typical cooling block is preferably made of stainless steel and has polished surfaces. These polished surfaces can also be used for tissue flattening chores. The cooling block should be big enough to fit over a chuck and cool the chuck and sample without significantly warming up itself. FIG. 6 depicts a cylindrical cooling block designed for a stemmed chuck. The block pictured is 50 mm in diameter by 38 mm in height, and has a hole 10 mm in diameter drilled through the block to accomadate a stem. The cooling blocks can also be rectangular shaped. For stemless chucks the attachment surface of the cooling block includes a female receiving end to attach to the attachment on the chuck. The thickness of the cooling block is large as compared to the face thickness of the chuck.

Since the cooling block is removed from the chuck and returned to a cool chamber after the sample is frozen, the cooling blocks will be maintained at a temperature suitable for freezing a sample. This enables the cooling block, even when placed upon a warm chuck, to effectively cool the chuck and extract heat from a sample through the chuck.

Figure 2:
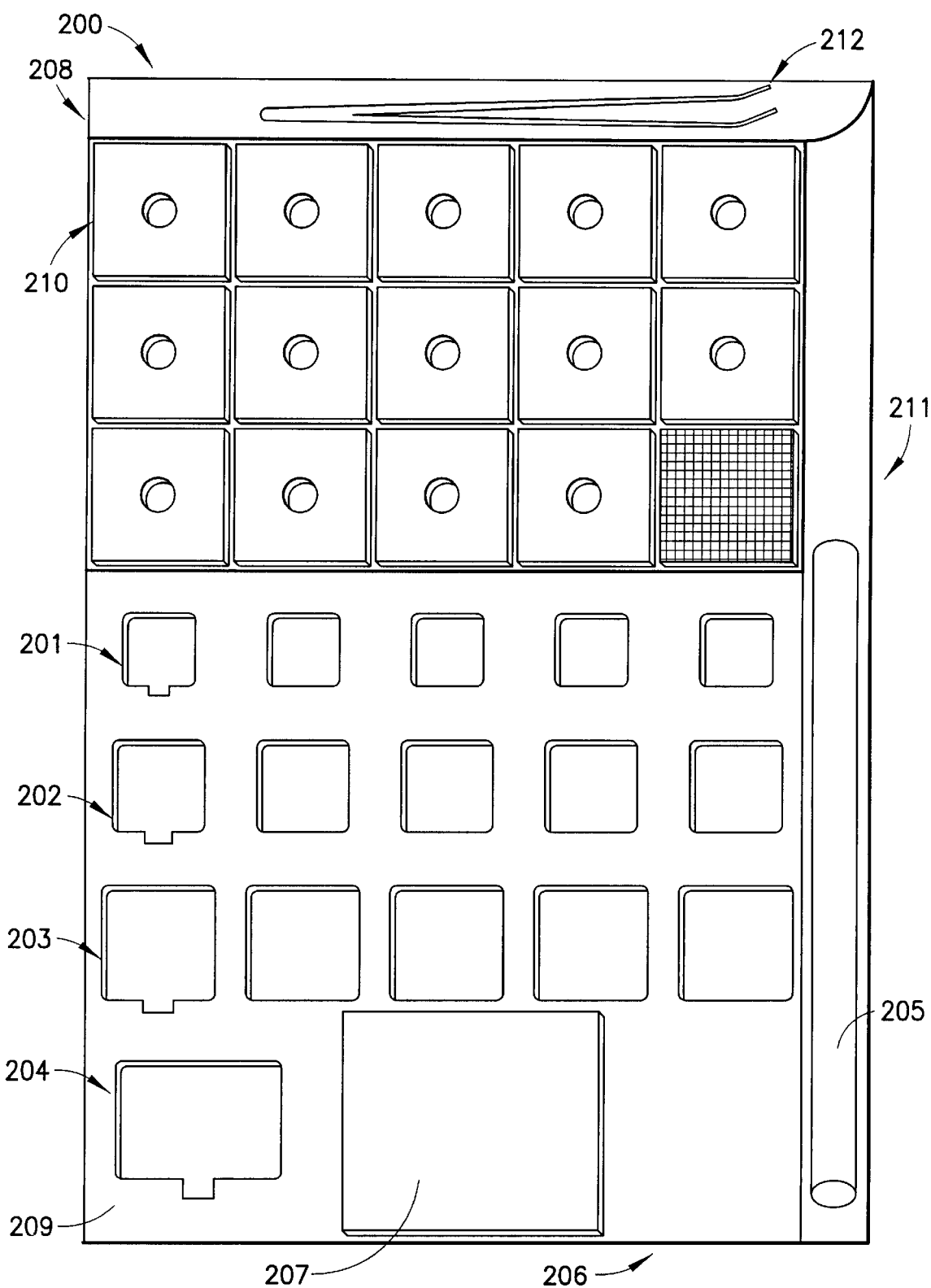
FIG. 2 depicts a top view of another preferred embodiment of a stand-alone cryoembedding center.

The dislodging tool serves to free the chuck and embedded sample from the well when tapped against the chuck stem or cooling block. The dislodging tool should be made of a material of sufficient weight and hardness that a sharp tap to a chuck or cooling block will free the chuck/embedded sample combination from the embedding well. The cold steel of the chuck face adheres tightly to the medium over the large surface area of the face, while the sharply cut channels require a large sheering force to break the bond between the chuck and the medium. Thus, when tapped with the dislodging tool, the chuck/frozen medium combination is easily removed from the well while remaining intact. A dislodging tool 205 is depicted in FIG. 2. The dislodging tool shown is a 12 mm in diameter by 200 mm long stainless steel rod.

The freezing plate, also referred to as the griddle, aids in frozen block embedding preparation, flattening, prefreezing and uncurling tasks. In a preferred embodiment, it is made of polished stainless steel and can be part of the platform surface or it can be a separate stainless steel bar. A freezing plate is depicted as reference number 206 in FIG. 2 and as reference number 1102 in FIG. 11. For ease of use, the freezing plate is at least about 40 mm wide.

Figure 11:
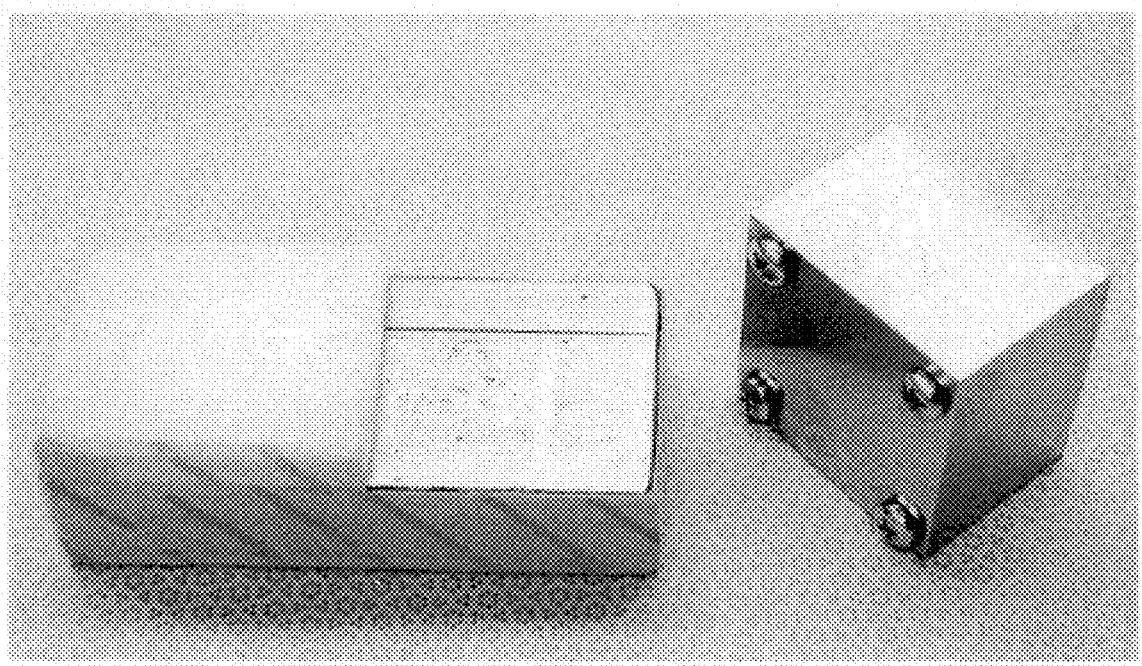
FIG. 11 depicts an elevated freezing block next to a bar with a freezing plate and a cutting board.

The cutting board can be attached either to the platform surface or on a separate bar adjacent to the freezing plate for use in cutting frozen blocks. Because the cutting board must be sterilizable, it should be made of a non-porous material such as plastic or metal. However, the cutting board should also be forgiving of cutting blades, so a plastic such as polyethylene is the preferred material. Again, for ease of use, the cutting board is at least about 40 mm wide. In one preferred embodiment depicted in FIG. 2, the cutting board 207 is 70×60 mm by 8 mm thick. Another cutting board 1101 is shown in FIG. 11.

Figure 12:
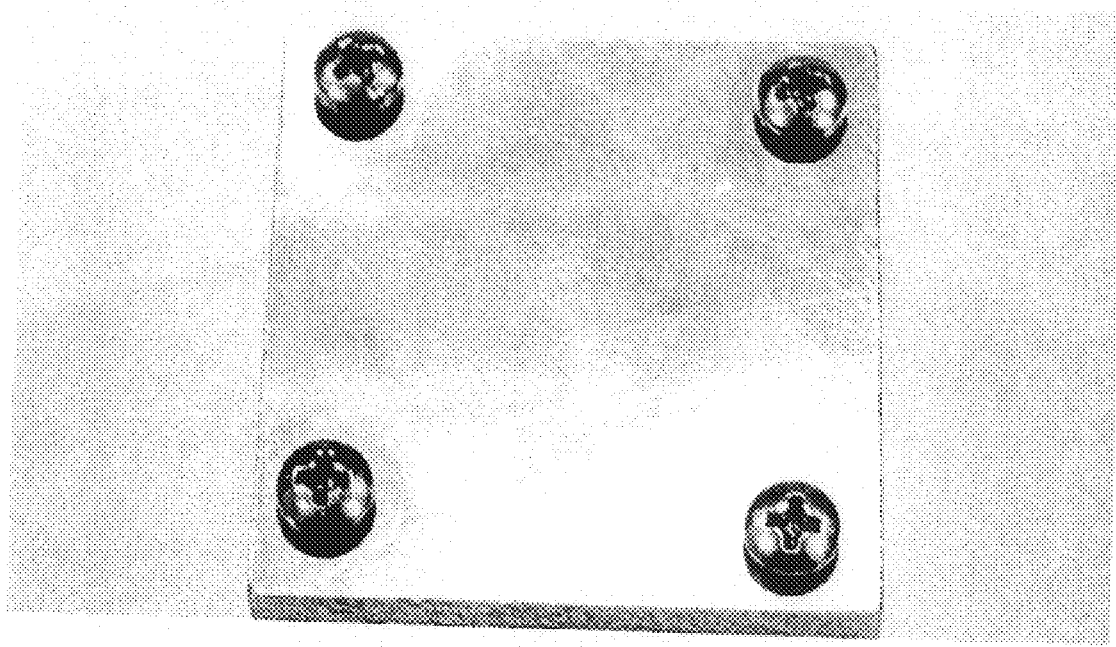
FIG. 12 depicts the footings of the elevated freezing block.

The elevated freezing block is preferably made of stainless steel with polished surfaces and has at least three, but preferably four, steel footings protruding from one surface. The freezing block can be applied to the surface of specimens on the freezing plate, freezing them to create a frozen block. The other flat surfaces of the freezing block can also function as additional freezing surfaces for use with plate or wells. The footings should be long enough to produce a sample that can be easily turned on side, which is about 3 mm long, but not so long that the sample does not freeze quickly, that is no longer than about 5 mm. The freezing block should be big enough to quickly freeze a sample. In a preferred embodiment, depicted in FIG. 11, the freezing block 1103 measures 50×50×38 mm and has four 4 mm long feet. This block can create a specimen 4 mm thick when applied to the freezing plate. The footings on the freezing block are depicted in FIG. 12. As shown, the footings can be the heads of screws screwed into the freezing block.

In another embodiment of the freezing block, a hole is drilled in the face opposite of the footings. This enables the freezing block to be placed on top of warmed chucks serving a duel function as an over chuck freezing block.

Figure 8:
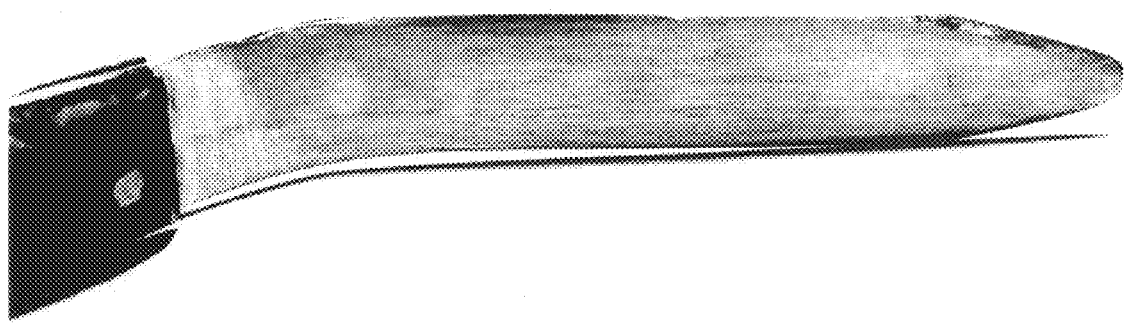
FIG. 8 depicts a spatula/prying tool.

The spatula/prying tool is used for removing frozen block cryoembedded specimens from the notched wells. The blade needs to be thin enough and sharp enough fit under a sample in a well, but thick enough to pry the sample out. The blade should be so sharp as to be medically dangerous. In a preferred embodiment, the prying tool has an angled stainless steel blade for ease of handling and the point of the blade forms a truncated angle. The edges of the blade are beveled and rounded at the edges. A typical prying tool is depicted in FIG. 8. The blade shown is about 1 mm thick, 12 mm wide narrowing to a width of 5 mm at the tip, and is bent at an angle of 30 degrees. The spatula/prying tool can also be used to lift an adherent specimen from the freezing plate.

The dispensing slide is a ruled, flexible slide that narrows at one end. It can be, for example, a flexible plastic ruler. Wetted tissue can be accurately dispensed into an embedding well from either end of the slide. In one embodiment, shown in FIG. 13, the slide 1301 is 200 mm long, 1 mm thick, with a width of 25 mm that narrows to 15 mm at the narrow end.

Figure 13:
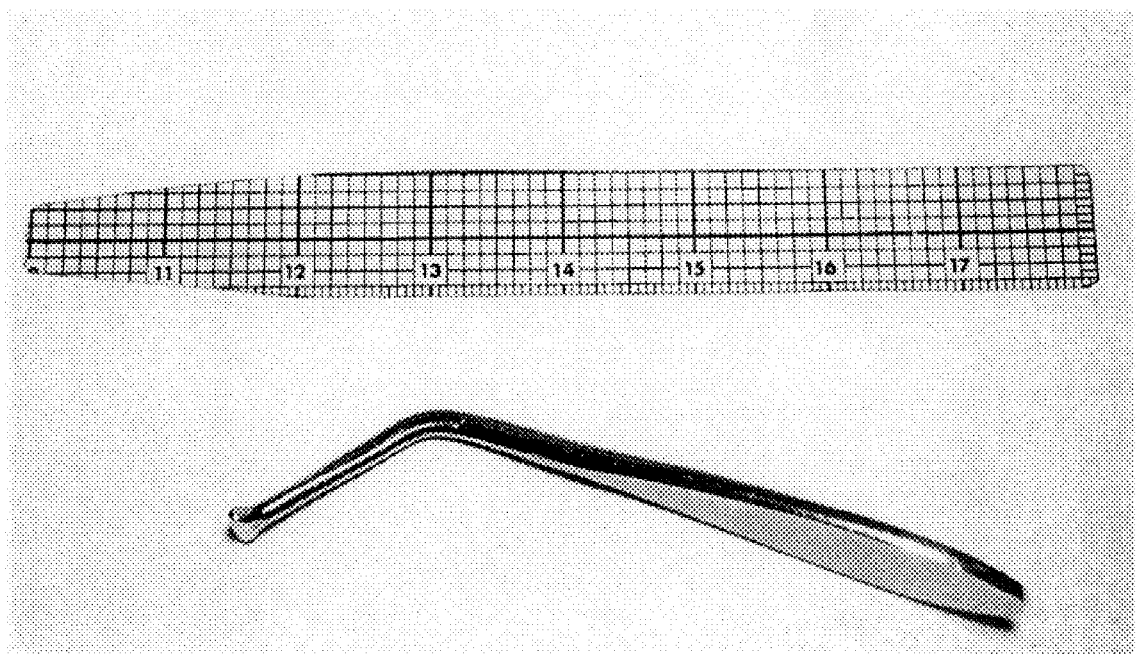
FIG. 13 depicts a tissue dispensing slide and a tissue flattening tool.
Figure 14:
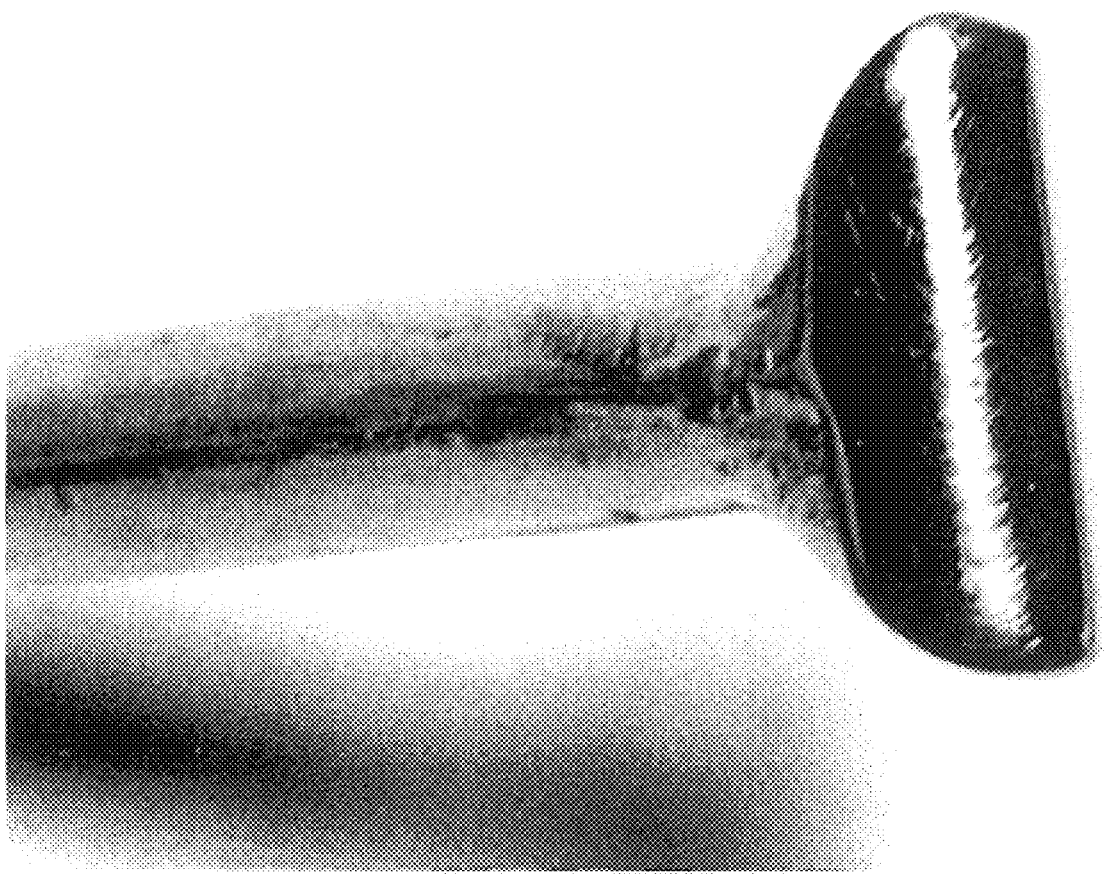
FIG. 14 depicts a close up of the bar at the end of the tissue flattening tool.

The tissue flattening tool is a cylindrical bar attached to a handle. Preferably, the cylindrical bar is polished. The handle can also be bent for ergonomic reasons. FIG. 13 depicts an exemplary flattening tool 1302. The tool 1302 is used to flatten tissue samples on the floor of the embedding well as the samples are slid off of the dispensing slide 1301. The cylindrical bar should be small enough to fit inside an embedding well. The tool should be used warm (i.e. at an above freezing temperature, such as room temperature) so that it does not stick to the tissues. In the embodiment shown in FIG. 13, the round bar 1303 measures 10×4 mm and is attached to the handle 1304, which is bent at an angle of 135 degrees. A close-up of the round bar is shown in FIG. 14.

Figure 1:
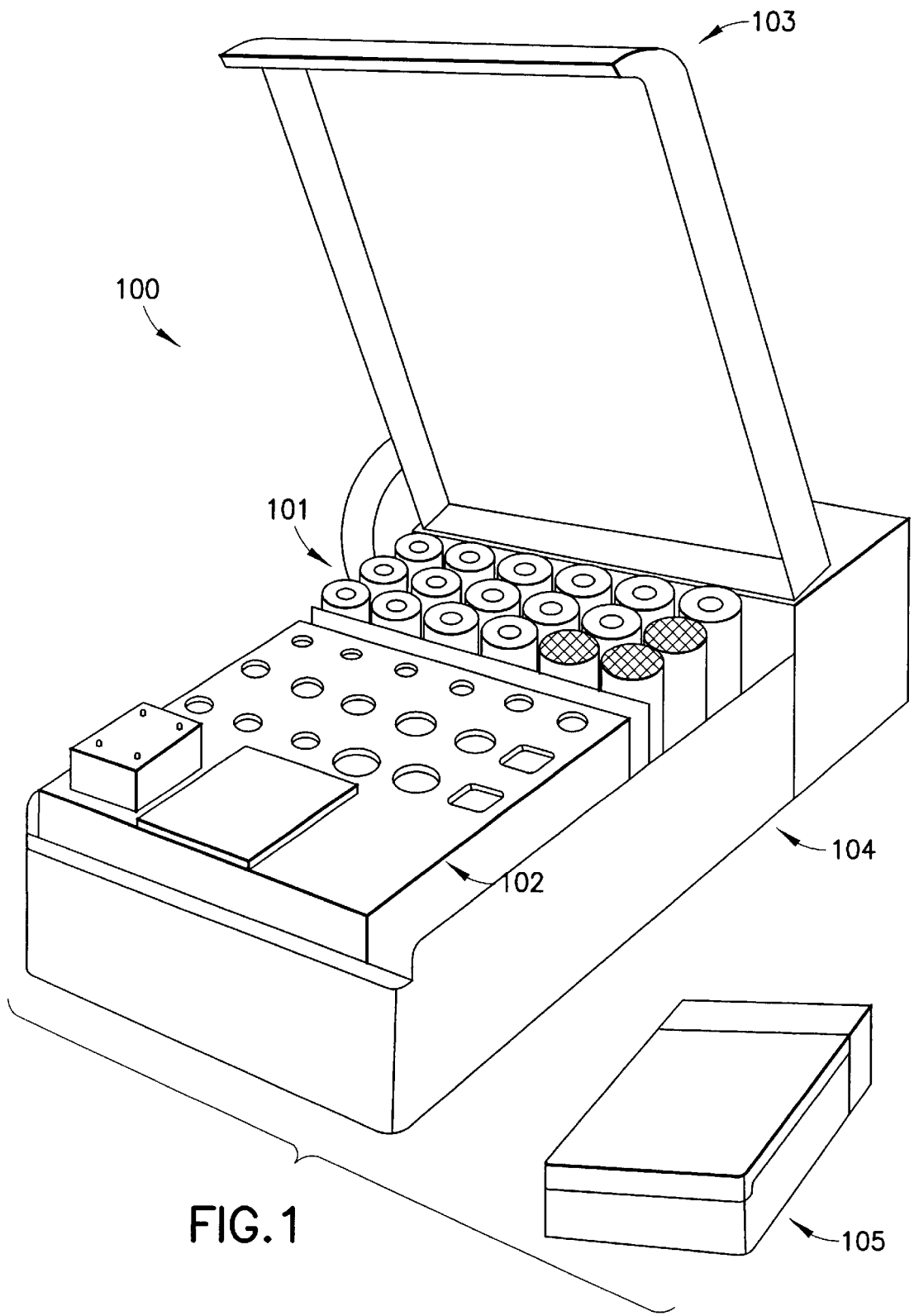
FIG. 1 depicts an isometric view of a preferred embodiment of a stand-alone cryoembedding center.

One embodiment of the apparatus of the invention is a stand-alone refrigerated cryoembedding center. A top view of a stand-alone center 200 is depicted in FIG. 2, and an isometric view of another cryoembedding center 100 is depicted in FIG. 1. This stand-alone center includes a work chamber (reference number 101 in FIG. 1, reference number 208 in FIG. 2) containing the above described components along with a work surface (reference number 209 in FIG. 2, reference number 102 in FIG. 1). The work chamber is cooled by a refrigeration compressor and cooling coils, while the work surface is cooled from beneath by a Peltier thermoelectric device, and the apparatus is set in an insulated housing. Temperature is regulated by a thermostat, and the apparatus is equipped with an electronic timing device to facilitate a defrost cycle.

One preferred embodiment of the stand-alone center, depicted in FIG. 2, measures 310 mm long by 220 mm wide by 60 mm high. The front of the work surface 209 from left to right contains a 30×45×4 mm embedding well 204, a 70×65 mm polyethylene cutting board 207 and a 60×65 mm freezing plate 206. The center 120×200 mm portion of the platform surface houses 15 embedding wells in rows 201, 202, 203, which in this example are square with corners rounded to a 4 mm radius and centrally spaced in areas 40×40 mm each. Wells that are 30 mm square and 4 mm deep are in the front row 203, 24 mm square wells 3.5 mm deep are in the center row 202, and 18 mm square wells 3 mm deep are in the rear row 201. The wells on the left column has 7×7 mm notches for use with the frozen block cryoembedding method described below. Immediately to the rear of the embedding wells is a 200×120 mm recessed area 210 that is 10 mm deep which houses 15 36×36×38 mm over chuck cooling blocks. Atop the cooling blocks chucks can be placed as described above. On the right side and rear is an instrument channel 211 that is 20 mm wide that has a rounded base and extends the length and width of the unit. This channel can house the dislodging bar 205, the spatula/prying tool (not shown), and a cooled forceps 212. The dimensions given here are exemplary, and a different sized cryoembedding center with different sized wells, chucks, etc., is still within the scope of the invention.

Referring now to FIG. 1, the top 103 of the stand-alone center hinges upon hydraulic supports and closes to make a tight seal by compressing a rubber insulation stripping pulled tight by a locking mechanism. A closed cryoembedding center 105 is shown in the figure. A molded insulated casing 104 houses the work surface, refrigeration and electronic devices. Temperature is regulated to stay in the −25 to −30 degrees C. range by a thermostat. A timing device allows a scheduled defrost period to be performed at a timed interval.

Figure 9:
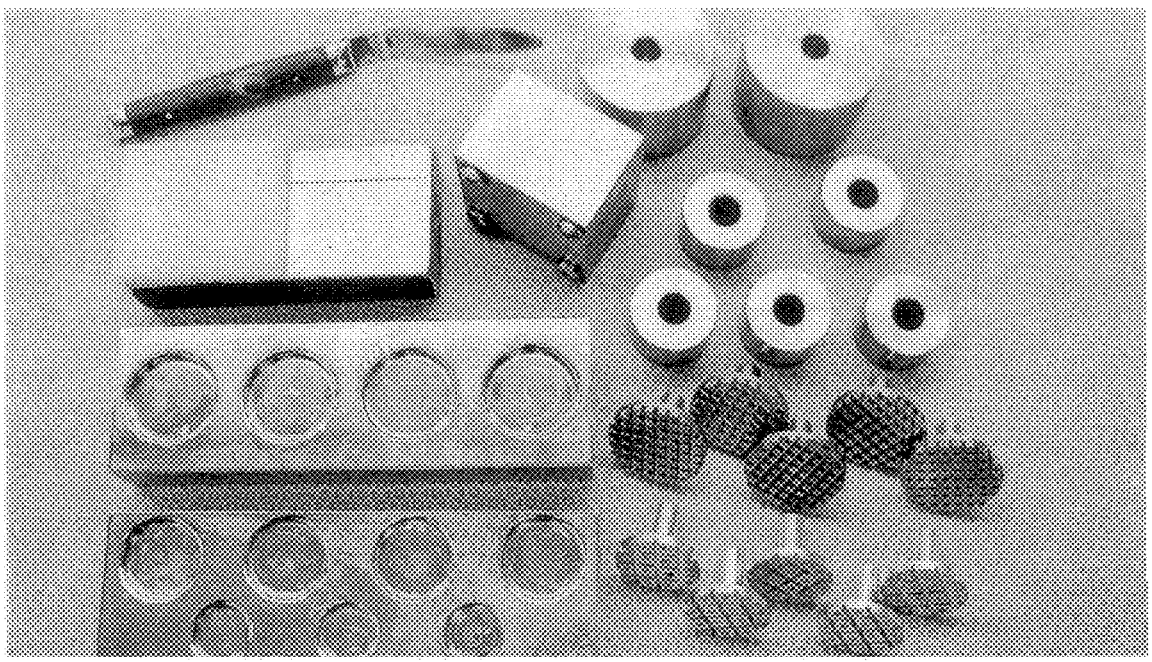
FIG. 9 depicts a set of portable modular well bars.

Another embodiment of the apparatus of the invention comprises a set of portable modular embedding well bars which can be refrigerated in a cryostat or other refrigerated chamber capable of cooling the well bars to −25 to −30 degrees C. The well bars should be big enough to stay cold, but not so big that they become hard to handle or lift. Two of these well bars 901, 902, are depicted in FIG. 9. The bars are preferably made of stainless steel and house embedding wells of varying sizes and combinations. The well bars shown measure 25 mm thick by about 60 mm wide.

Another component is a separate stainless steel bar 903 25 mm thick and measuring 65×135 mm that has a polished surface 904 and includes a 70×65 mm attached polyethylene cutting surface 905. This bar will function as the freezing plate and cutting board as described above and can be used as a portable unit outside the refrigeration chamber for limited periods of time for ease of cutting and handling. Once again, the dimensions of the bars 901, 902, and 903 are exemplary, and differently sized bars are within the scope of the invention.

In addition, chucks 906, over chuck freezing blocks 907, the elevated freezing block, the dislodging bar (not shown), spatula/prying tool 909, dispensing slide (not shown) and flattening tool (not shown) can all be used as described above and stored in receptacles within a freezing chamber such as a cryostat or freezer.

Figure 10:
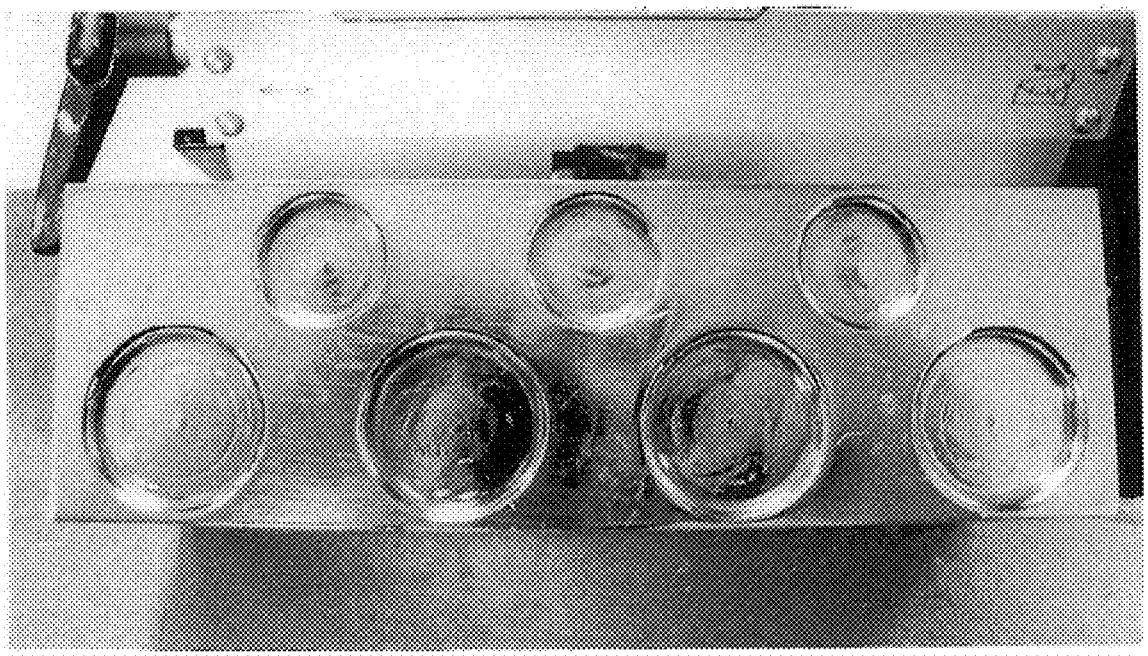
FIG. 10 depicts a well bar modeled to fit in a cryostat.

A third embodiment of the apparatus of the invention involves modeling the system components as described above into an embedding area of built-in design in the manufacture of a cryostat. Various combinations of well sizes, chuck design and over-chuck freezing blocks can be customized to the requirements of a particular instrument. An example of such an embedding area is shown in FIG. 10.

Figure 15:
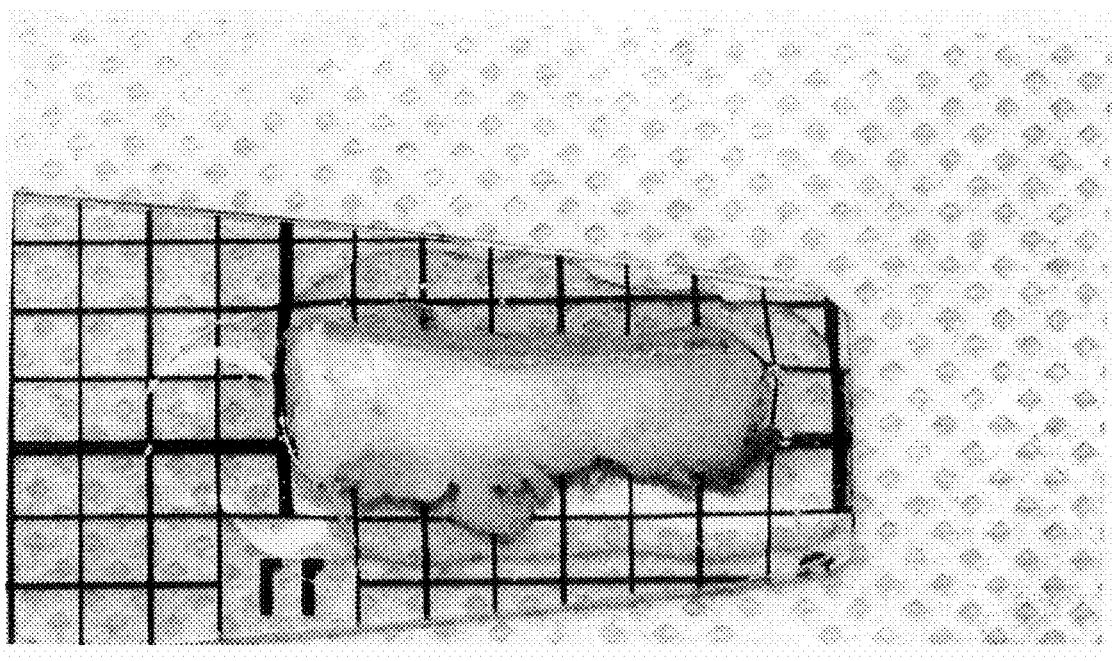
FIG. 15 depicts a tissue sample at the end of the dispensing slide.
Figure 16:
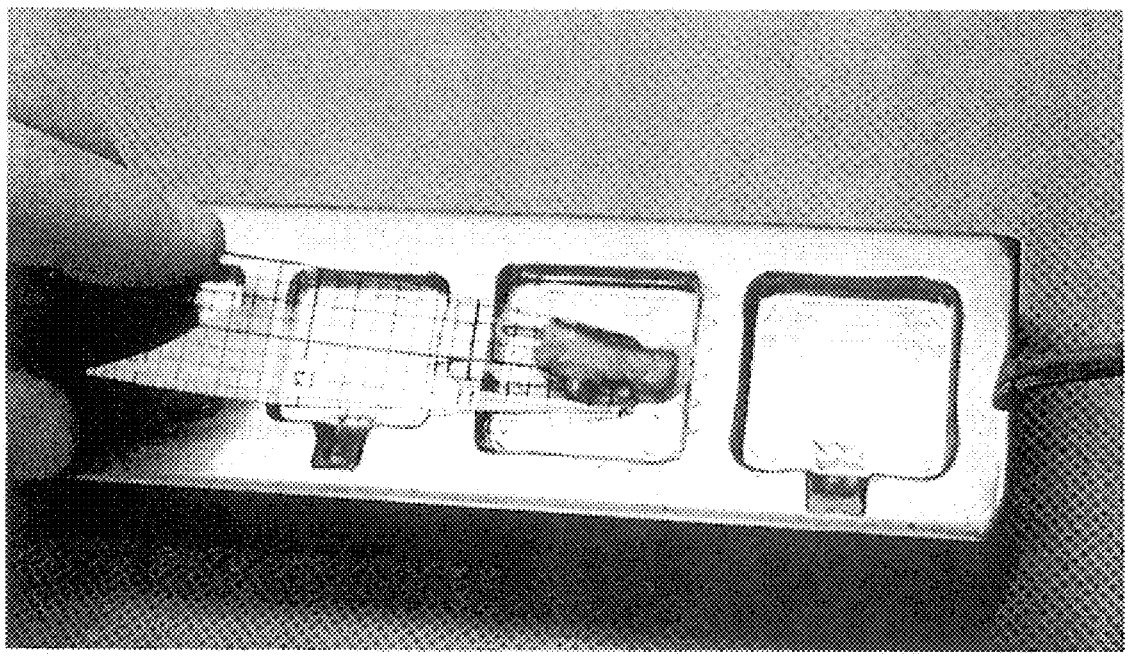
FIG. 16 depicts a sample being placed in a well.
Figure 17:
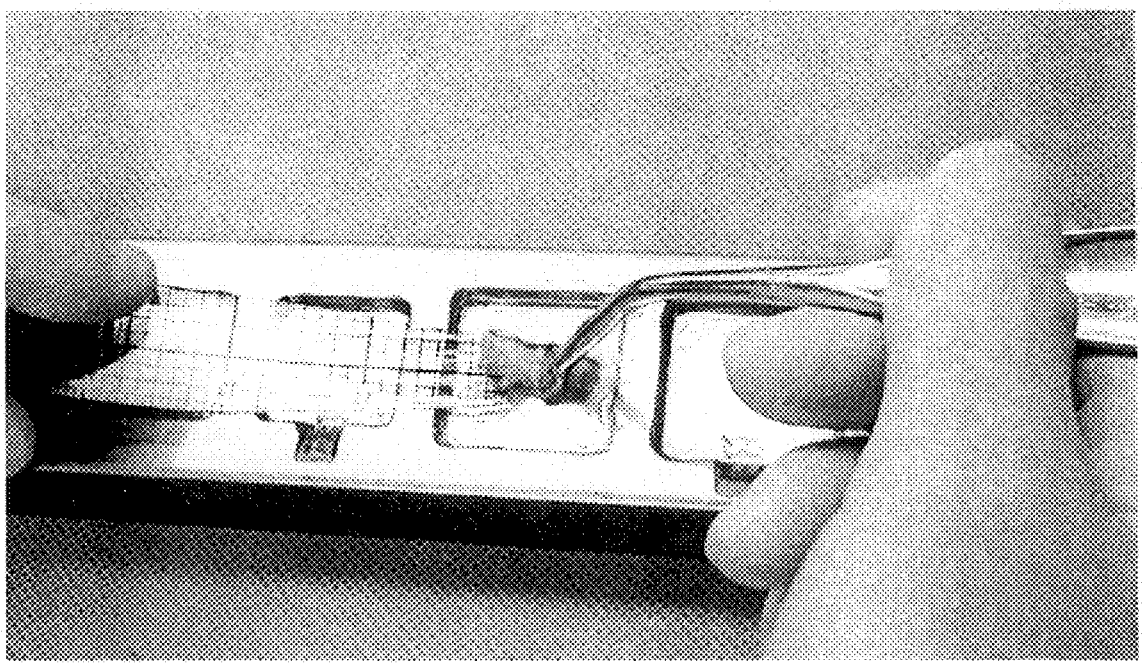
FIG. 17 depicts a tissue sample being flattened with the flattening bar as it is pulled from the dispensing slide.

A second aspect of the present invention is a method for preparing tissue samples using the system components described above. A first embodiment of the method comprises wetting a tissue sample with a drop of embedding medium and then placing the tissue sample cutting face down on the floor of the cooled embedding well. This is accurately accomplished by placing the wetted sample at either end of the dispensing slide, as shown in FIG. 15. In a preferred mode of operation, the tissue overlaps the edge by about 1 mm. Referring now to FIG. 16, the slide is placed over the desired site in the well and the overhanging edge is pressed to the well floor to which it adheres. In a slow motion the dispensing slide is pulled out from under the tissue, as shown in FIG. 17, and is simultaneously flattened with the flattening tool as the sample is pulled off of the slide. The gentle friction of the slide against the tissue applies a gentle stretching force as the flattening tool presses it to the floor. This process is analogous to wallpaper being flattened by a papering brush.

The tissue sample adheres to the floor of the well as a result of the cold temperature and is easily manipulated, stretched or flattened to yield the precisely desired cutting face.

Figure 18:
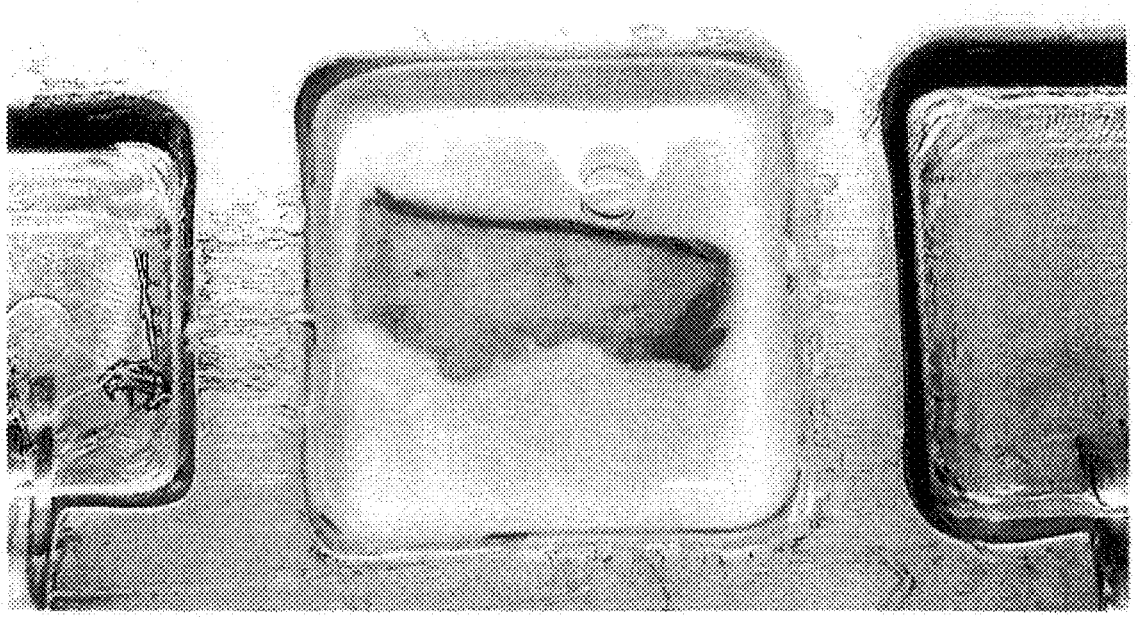
FIG. 18 depicts the tissue sample in the bottom of a well which has been filled with embedding medium creating a bulging meniscus.
Figure 23:
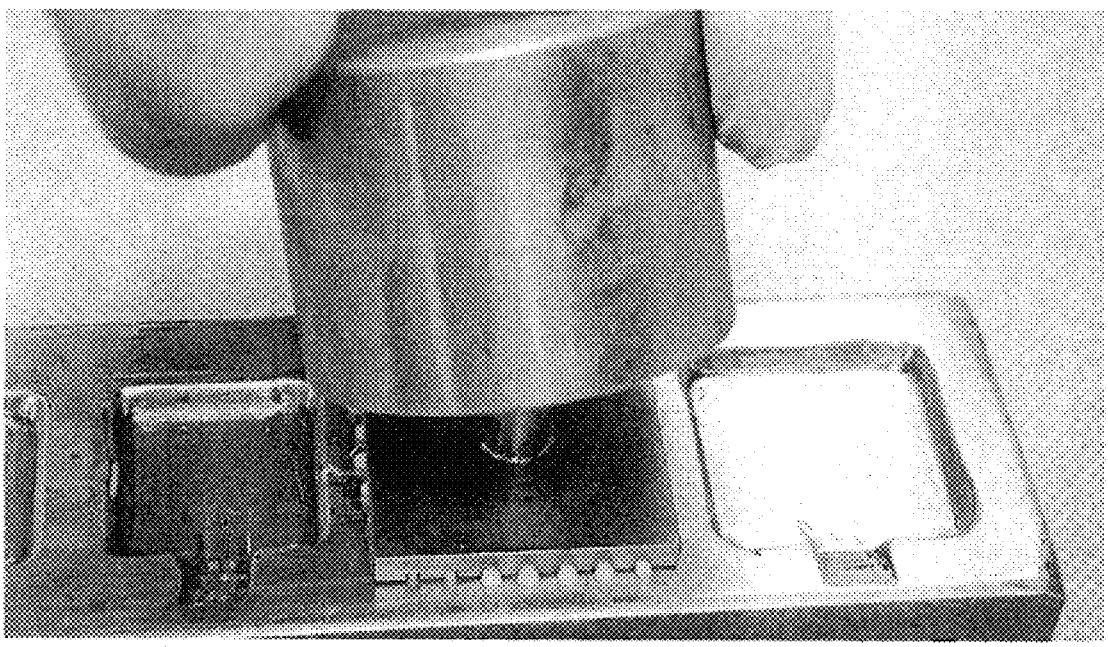
FIG. 23 depicts a cooling block being placed over a chuck stem.

Next, the well is filled with embedding medium to the brim creating a fluid meniscus that protrudes above the level of the well due to its viscosity and surface tension. FIG. 18 depicts a tissue sample adhering to the bottom of the embedding well after being filled with embedding medium. FIG. 19 depicts a chuck being placed face down onto the protruding meniscus, so as to cover the well. By virtue of the chuck design, excess embedding medium extrudes from the edge of the chuck as its placed flat on the steel platform face of the well. FIG. 20 depicts a chuck placed over a filled well, with excess embedding medium extruding from the channels. Next, an over chuck cooling block is either placed over the chuck stem or attached to a stemless chuck. FIG. 23 depicts an over chuck cooling block being placed over a stemmed chuck. The large size of the cooling block relative to the chuck face thickness, along with the cold temperature of the cooling block, enables the cooling block to cool the tissue sample. In a preferred embodiment, the cooling block is maintained at a temperature of −25 to −30 degrees C.

Figure 24:
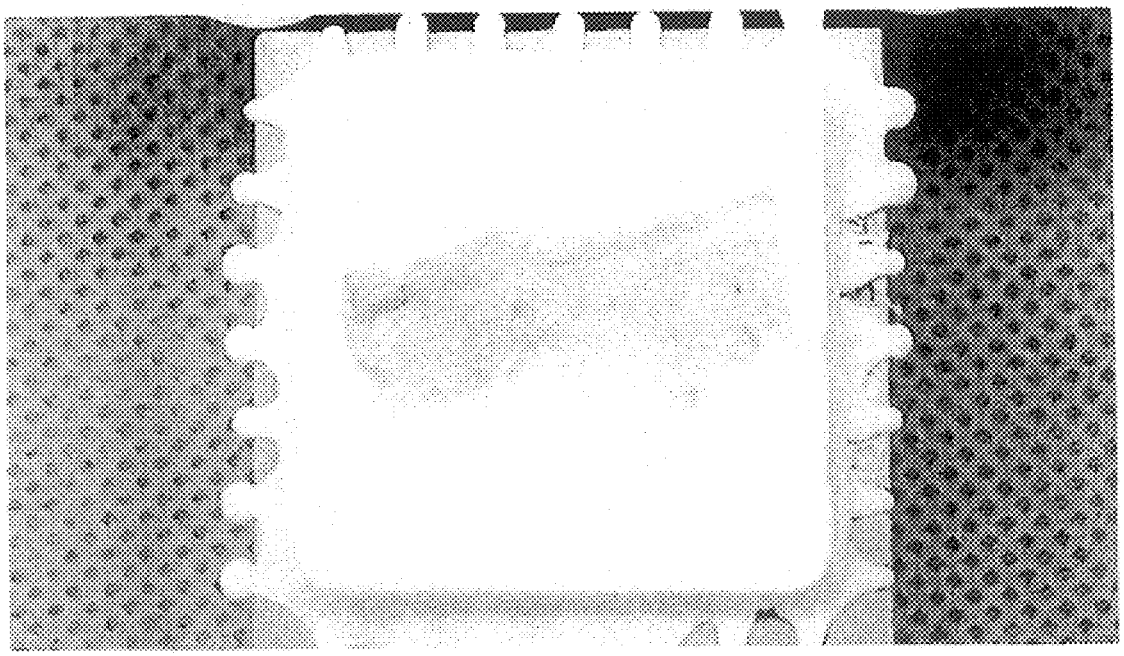
FIG. 24 depicts a frozen tissue section with a flat specimen face attached to a chuck..
Figure 27:
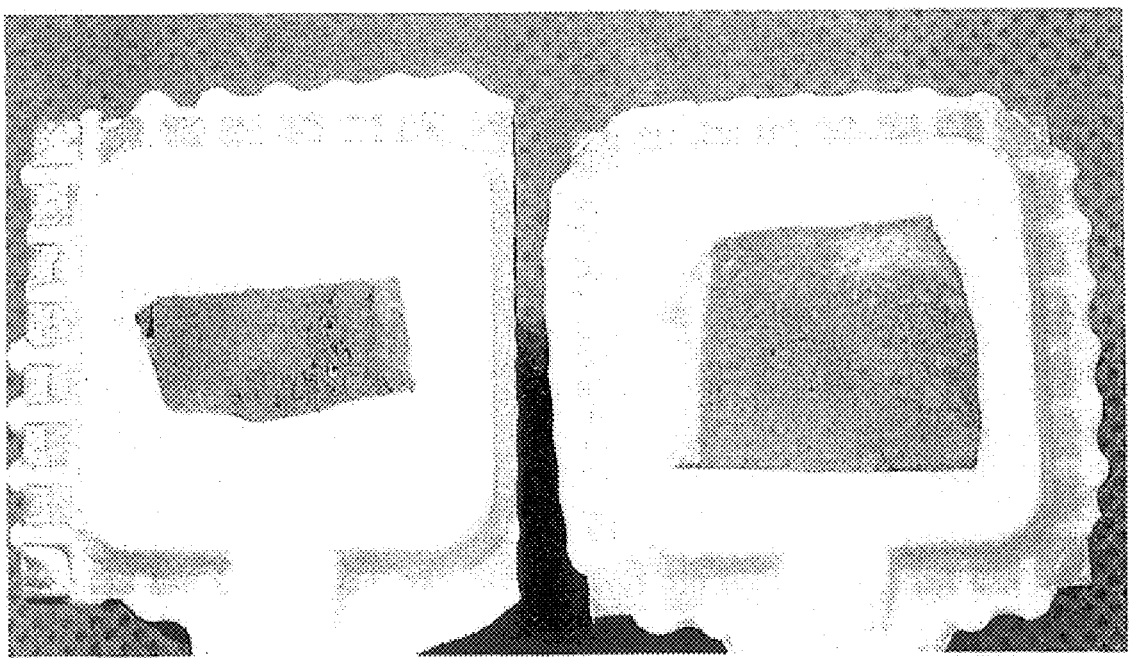
FIG. 27 depicts two frozen tissue preparations with flat specimen faces requiring little trimming attached to a chuck faces.
Figure 28A:
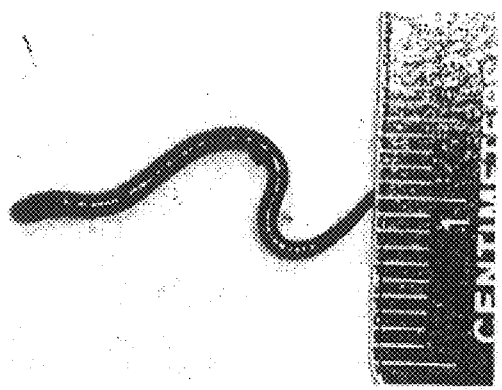
FIGS. 28a–28d depict Frozen Block Cryoembedding on a tubular sample, here a worm.
Figure 28B:
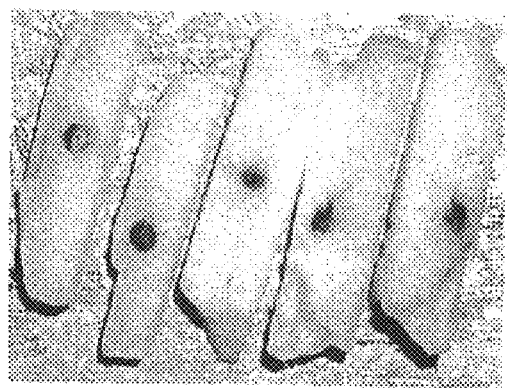
Figure 28C:
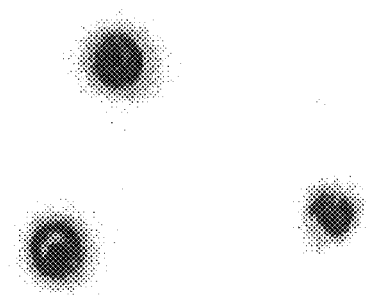
Figure 28D:
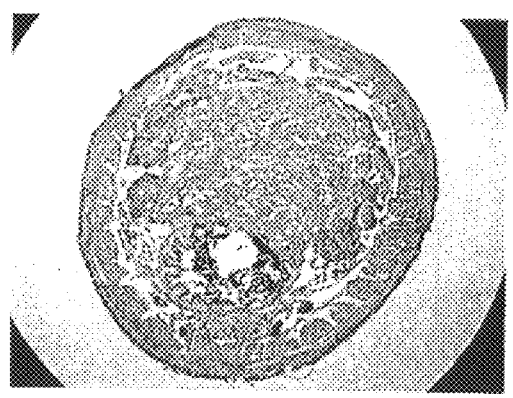

After a period of freezing which varies from less than 20 seconds to one minute depending on the temperature of the apparatus and the volume of the well and tissue, the chuck stem or over chuck cooling block is tapped with the dislodging bar easily freeing it. The chuck stem can also be tapped with a cooling block. The resulting preparation, examples of which are shown in FIGS. 24 and 27, has a flat surface parallel to the face of the chuck with the complete cutting face of the tissue visible. The block is of consistently similar thickness and has its face in the same plane as the chuck face, minimizing tissue trimming and wastage and chuck holder plane adjustment.

Figure 7A:
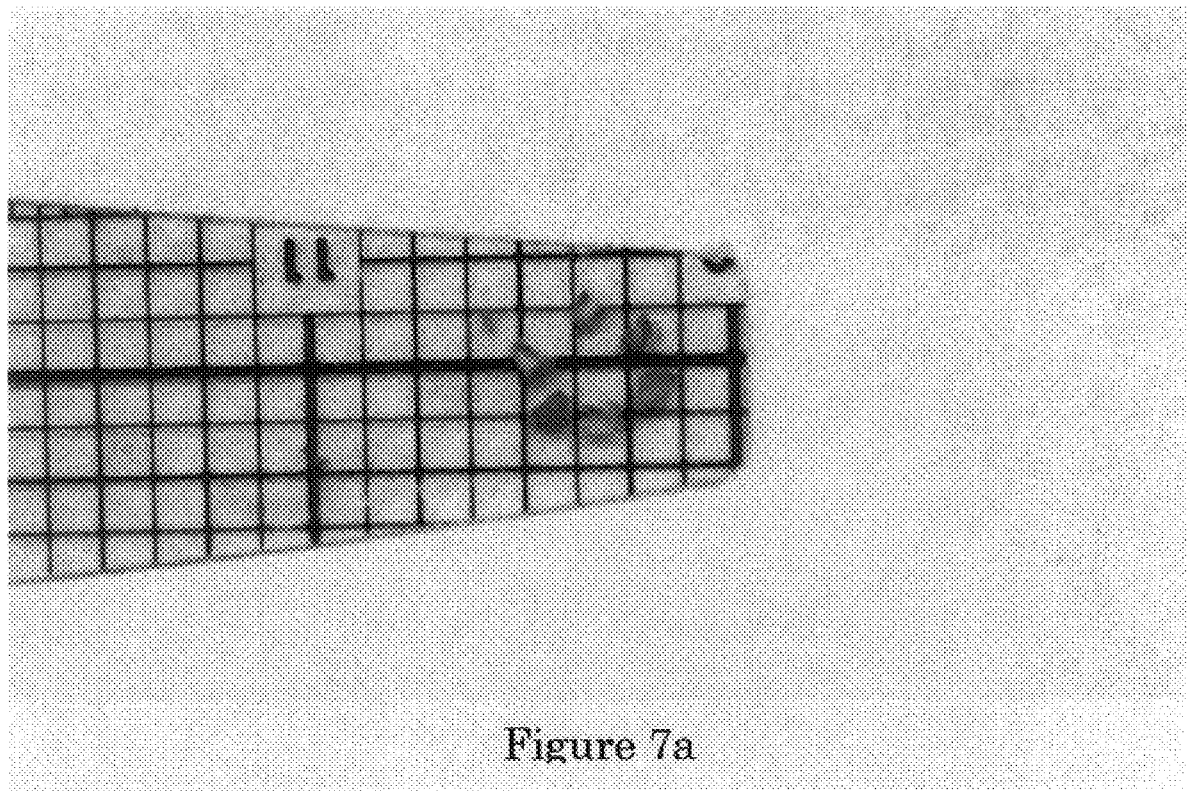
FIG. 7a depicts a sample in multiple small biopsy fragments.
Figure 7B:
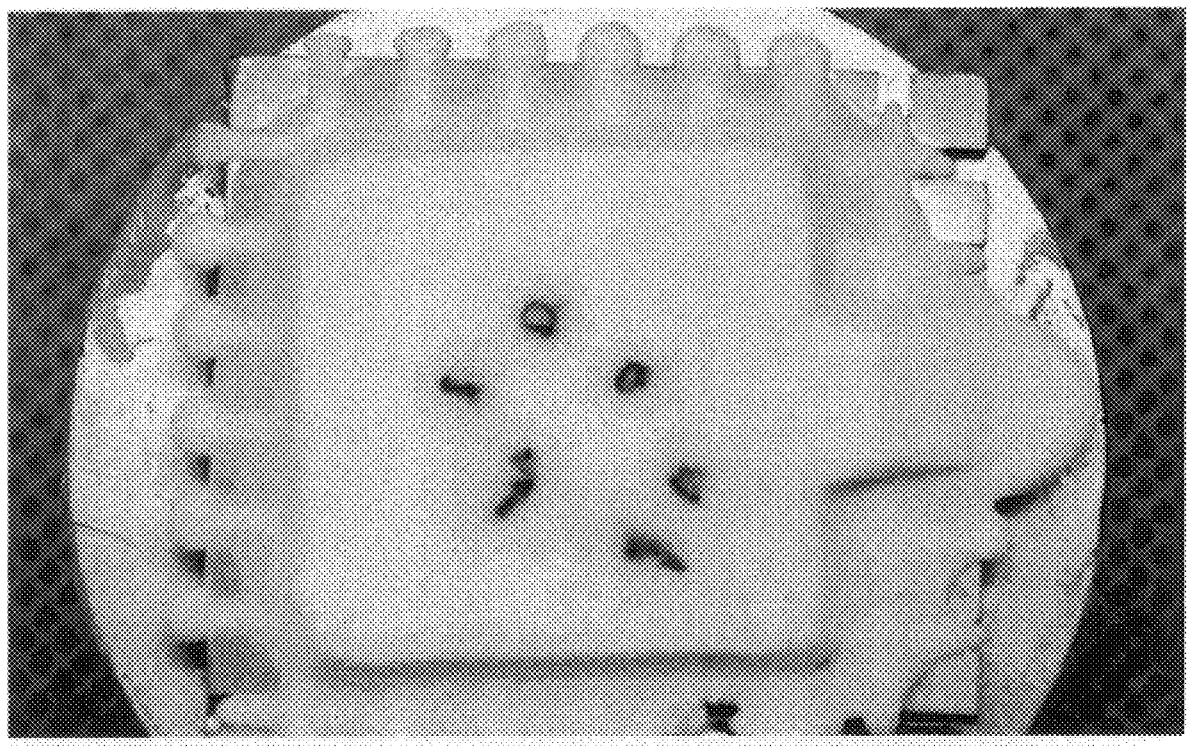
FIG. 7b depicts the small biopsy fragments in a trimmed completed preparation all embedded in a flat plane.

Another illustration of a specimen prepared by this method, demonstrating how this invention minimizes tissue wastage, is depicted in FIGS. 7a and 7b. FIG. 7a shows six minute biopsy samples on the dispensing slide. The size can be compared with the ⅛ inch grid on the dispensing slide. Small samples such as these can be slid off the slide with a forceps or equivalent device. FIG. 7b shows the completed sample after embedding and trimming. All six samples have been frozen and embedded in the same plane and can be sectioned onto the same slide. Slides can be made for this level of trimming precision while preserving the remaining tissue for formal preparation, such as paraffin embedding, and other studies. Using conventional methods of tissue preparation, it is very possible the entire specimen would be lost attempting to reach the more deeply buried samples.

A second embodiment of the method of the invention is a method for preparing tissues referred to herein as "Frozen Block Cryoembedding". This method uses the apparatus described herein for precise orientation and handling, including the most difficult embedding situations. These situations include: (1) minute samples requiring precise orientation for resection margin assessments; (2) extremely thin, flat, or tubular tissues requiring an on-edge orientation; (3) perforated, torn or friable samples requiring precise orientation or resection margin assessment which would immediately result in minute, virtually impossible to orient fragments when cut with a scalpel; and (4) rubbery, curled specimens or angular or curved specimens requiring flat embedded faces to adequately assess the sample.

Figure 21A:
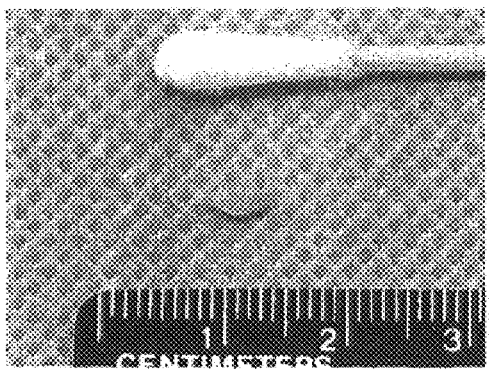
FIGS. 21a–21h depict Frozen Block Cryoembedding on a minute skin sample.
Figure 21B:
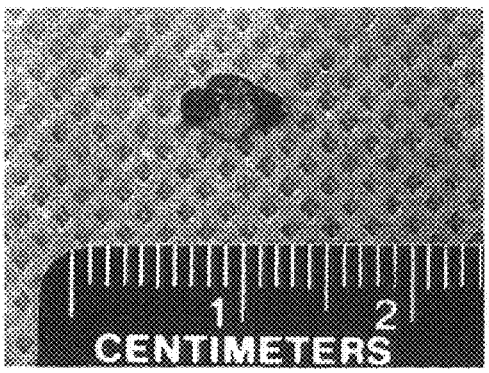

A typical minute skin specimen requiring orientation and resection margins is depicted in FIGS. 21a to 21h. FIG. 21a shows a 3×2 mm skin sample. FIG. 21b shows the specimen after four colors of ink are applied to demonstrate the margins of resection, i.e., the edge of the specimen. Each color stands for a different margin. For instance if it were the tip of the nose, red could mean superior (toward the head)

yellow could mean inferior (toward the feet) green could mean left and blue could mean right). If the pathologist finds the tumor extends into the ink under the microscope, he can inform the surgeon that the tumor has not been adequately excised.

Figure 21C:
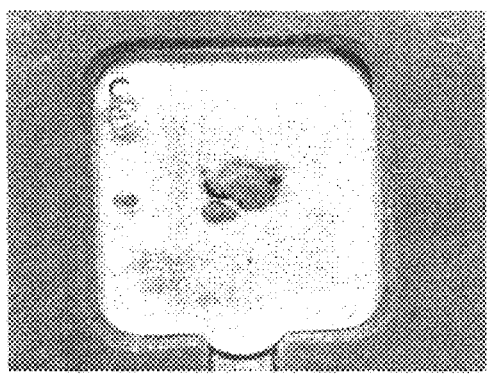
Figure 21D:
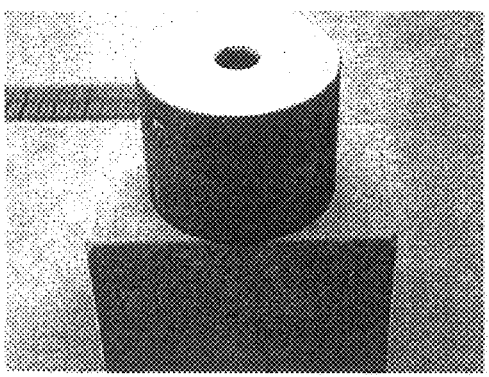
Figure 21:
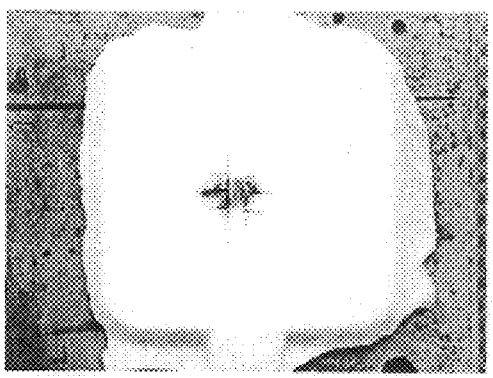
Figure 25:
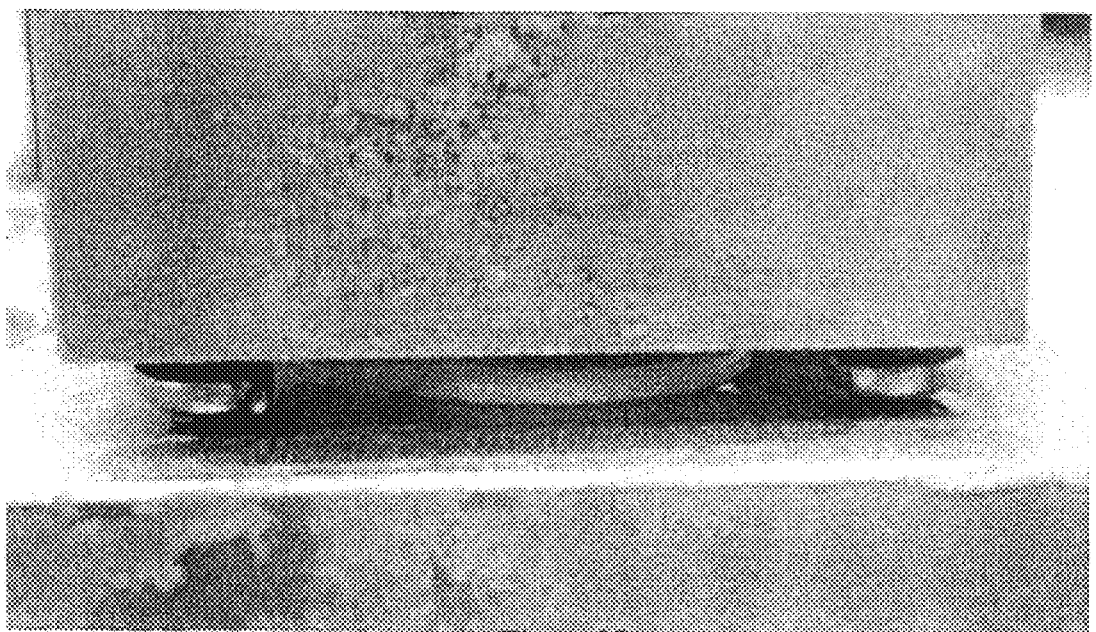
FIG. 25 depicts a freezing block on top of a specimen.

The first step of this method involves coating the specimen with embedding medium and placing it into either the notched embedding well or onto the freezing plate in such a way that the surface to be approached with the cutting scalpel is face down. If the well is used it is filled with embedding medium after which the flat surface of a cooling block is placed over the well. FIG. 21c shows the tumor on the floor of the well that has been filled with embedding medium. FIG. 21d shows a freezing block placed flat surface down over the filled well. If the freezing plate is used the sample is covered and surrounded with embedding medium and the undersurface of the elevated block is placed over the specimen. An elevated freezing block on top of a specimen is depicted in FIG. 25.

After a brief freezing period the freezing block is removed. The lightly frozen block encasing the specimen is placed on the cutting board. FIG. 21e depicts a specimen in a frozen block that can be easily sliced (the lines scored for demonstration show the path of the scalpel). The frozen specimen block is tested with a scalpel cut to assure that it is frozen, but not so hard that it would shatter or fly apart upon being cut. If the sample is frozen too hard it can be warmed with a gloved hand or allowed to warm for a brief period at room temperature until it cuts easily.

Figure 21F:
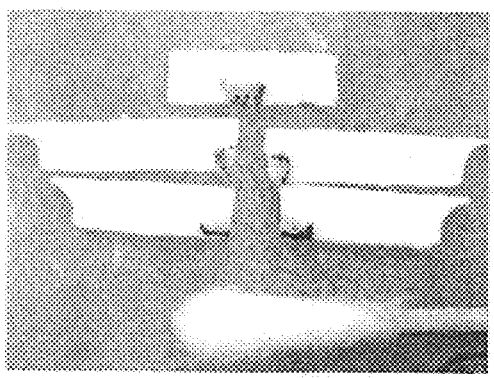
Figure 21G:
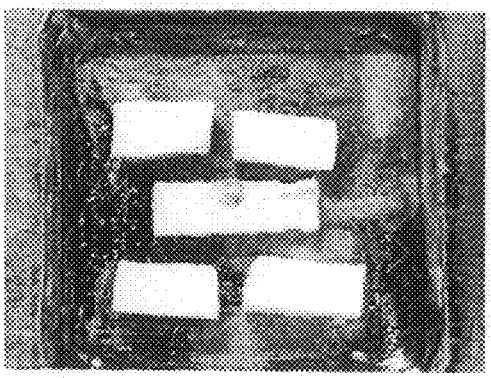
Figure 21H:
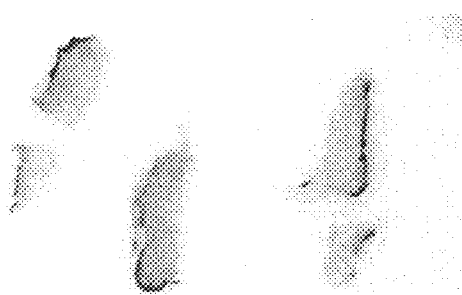

The frozen block is now easily sectioned with the scalpel in the desired planes. By virtue of being embedded in a block of embedding medium the specimen is now firm and cuts into flat pieces easy to turn on side. FIG. 21f depicts the slices of the frozen block turned 90 degrees face up for illustrative purposes. These minute pyramidal fragments (compare the cotton swab for a size reference) need to be embedded in a freezing liquid medium, turned on side and oriented in three dimensions, preferably with skin surfaces parallel for optimum preparation. By conventional methods this is nearly impossible. Using Frozen Block Cryoembedding this is accomplished easily and reliably. Specimens that were originally small or flat are now greatly enlarged in dimension yielding larger and flatter fragments that are easy to handle. FIG. 21g shows the slices placed face down in the well, easily placed in line. The well is now filled and the chuck is placed to complete the preparation. FIG. 21h depicts a completed trimmed frozen section block preparation precisely frozen and embedded on edge with all inked margins in optimum orientation.

Figure 26:
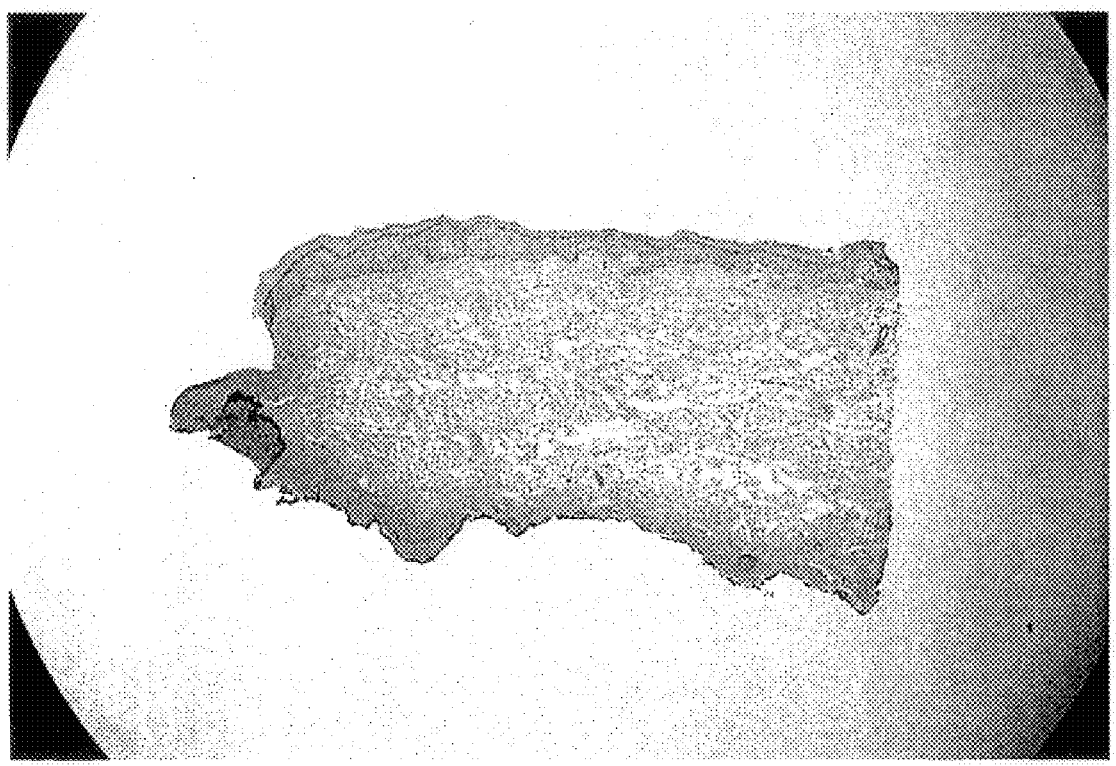
FIG. 26 depicts a microscopic section of on of the longitudinal margins from a minute skin biopsy as in FIG. 21.

FIG. 26 shows a microscopic view of one of the smaller pyramidal shaped margin fragments. The section is perfectly oriented on edge with the epidermis seen as the darker surface above and the ink visible on the margin at the base and side. The sharply cut side on the right is where the scalpel cut the section way from the central slice.

Figure 22A:
FIGS. 22a–22d depict Frozen Block Cryoembedding on a perforated skin sample
Figure 22B:
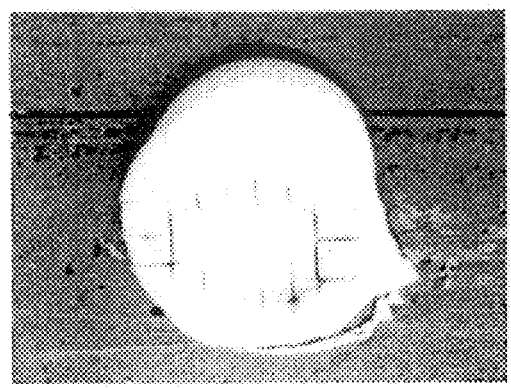
Figure 22C:
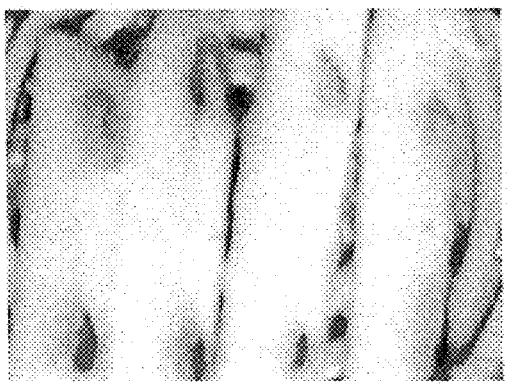
Figure 22D:
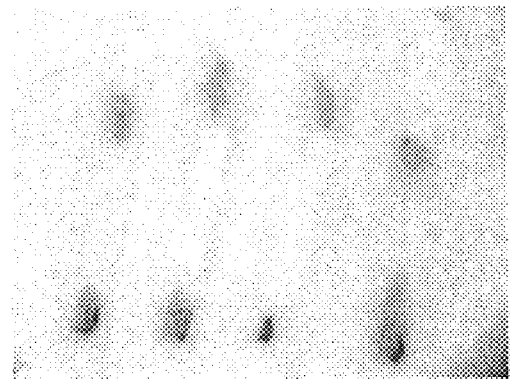

FIGS. 22a to 22d depict Frozen Block Cryoembedding applied to a perforated skin sample. FIG. 22a shows a skin biopsy which earlier had a central portion removed. The specimen must be inked, embedded on edge and oriented so that sections will demonstrate margins. FIG. 22b shows the sample in a frozen block of embedding medium (the scored lines show the path of the scalpel). FIG. 22c show the slices of the block turned on edge. FIG. 22d shows the completed preparation. Orientation is maintained. The central perforation is apparent between the yellow and red stained margins. Were the fragments not held together in this frozen block the sample would form a myriad of small fragments upon slicing. It would be difficult to determine which side of each fragment was the margin side and which was the perforation side, and simply turning the fragments on edge would be a feat.

FIGS. 28a to 28d demonstrates Frozen Block Cryoembedding applied to a flimsy tubular specimen, here a 1.5 mm worm, allowing perfect cross sections to be obtained.

Figure 29A:
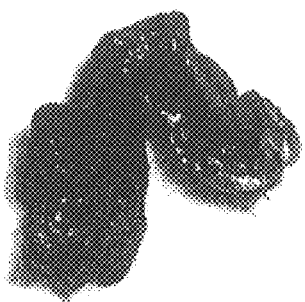
FIGS. 29a–29d depict Frozen Block Cryoembedding applied to a rubbery curved specimen.
Figure 29B:
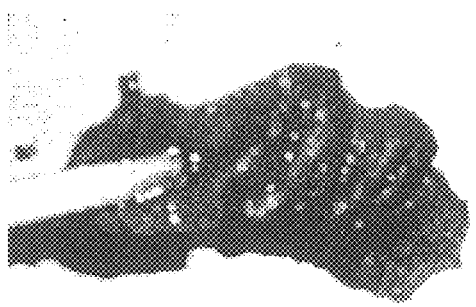
Figure 29C:
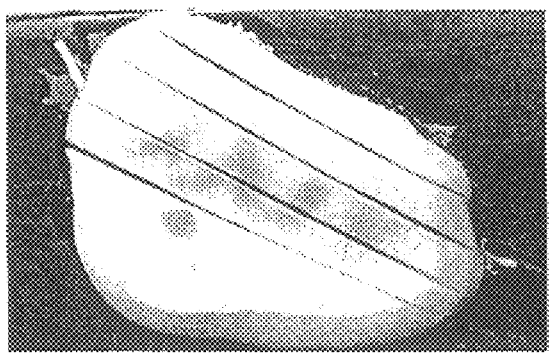
Figure 29D:
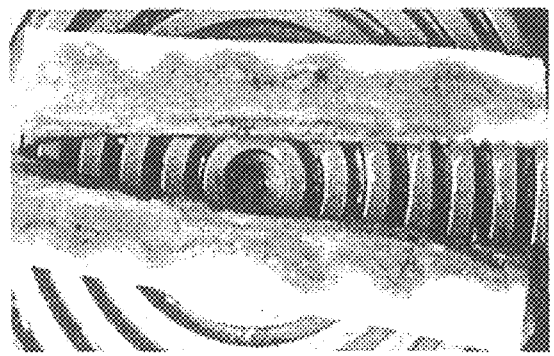

Specimens with angular, curled or irregular surfaces requiring flat embedded faces can also be prepared using the flat freezing plate or the flat surface of a freezing block. By virtue of the adhering properties of metallic surfaces cooled to −25 to −30 degrees C., the specimen can be stretched and flattened by either manipulating it with the flattening tool, the forceps, or by compressing it with freezing blocks. FIGS. 29a to 29d demonstrates Frozen Block Cryoembedding on a rubbery folded specimen. FIG. 29a depicts a folded rubbery portion of colonic tissue requiring embedding on edge while stretched out. FIG. 29b depicts the edge of the specimen adhering to the freezing metal plate allowing it to be pulled, stretched and flattened by adhesion to the plate. FIG. 29c depicts the colonic tissue covered with embedding medium on the freezing plate and scored to show the path of the scalpel. FIG. 29d shows the sliced specimen, demonstrating perfect transverse cutting and displaying all layers of the bowel wall. These flattened and transversely cut slices can then be placed face down in the embedding wells and prepared as described above.

The system of the invention is not limited to the embodiments disclosed herein. It will be immediately apparent to those skilled in the art that variations and modifications to the disclosed embodiment are possible without departing from the spirit and scope of the present invention. In particular, the dimensions of the components and the free-standing cryoembedding center presented herein are illustrative only, and different sized components or free-standing centers are still within the scope of the invention. Deeper embedding wells can be used, for example, to create a tissue block for storage, and a cryoembedding system intended for research purposes rather than clinical usage could use larger sized components. The shape of the components are also illustrative, and, for example, circular shaped embedding wells and chucks can be used and are within the scope of the invention.

Metals, because of their heat conducting qualities, are generally the preferred materials for those components directly involved in freezing the tissue sample, i.e. the platform and work surfaces, chucks, cooling blocks, freezing block and freezing plate. A preferred metal should also be non-corrodible and easily polished. Although the embodiments described herein utilize stainless steel, other metals, such as aluminum, copper, or bronze, could easily be used.

The temperature range used for cryoembedding samples should be sufficiently cold so that samples adhere to the surfaces, but not so cold that adhesion breaks down. The inventor has found, for example, that the minimum temperature for a sample to adhere to stainless steel is about −5 to −6 degrees centigrade, and that at temperatures below about −40 to −45 degree centigrade, tissue samples stop adhering to the metal surface. In addition, excessively cold samples freeze too quickly and shatter when cut. In fact, even though the cryoembedding is carried out at a temperature that is preferably about −25 to −30 degrees centigrade, the preferred temperature for cutting is about −20 degrees C.

Although a rectangular grid pattern is preferred for the channels cut in the chuck face, other patterns are within the scope of the invention. For example, the channels can also form a triangular grid, or the channels can radiate from the center of the chuck. The channels can also be a series of concentric circles, as shown in the chuck depicted in FIG. 29d. This pattern is not optimal, however, as it blocks extrusion of the embedding medium.

The invention is defined by the appended claims.

What is claimed is:

1. A kit for embedding and rapidly freezing tissues for frozen sections, comprising:
   a metallic platform having one or more embedding wells adapted to hold a tissue sample, each embedding well having a floor so that a tissue sample can be placed on the floor of any said embedding well and be covered with an embedding medium;
   one or more metallic chucks, each said chuck adapted to be applied flush to the surface of the metallic platform to cover an embedding well containing a sample covered with embedding medium, said chuck being adapted to adhere to the embedding medium; and
   one or more metallic over-chuck cooling blocks adapted to be placed on top of said chucks to extract heat from said chucks to aid in forming a frozen sample.

2. The kit of claim 1, wherein the metallic platform comprises a flat polished surface.

3. The kit of claim 2, wherein the metallic platform is made of stainless steel.

4. The kit of claim 1, wherein each embedding well is polished.

5. The kit of claim 1, wherein the embedding well comprises beveled walls, wherein the top of the embedding well is wider than the bottom of the embedding well.

6. The kit of claim 5, wherein a bevel of the the beveled walls comprise an angle of in the range of 95 to 135 degrees with respect to the base of the embedding well.

7. The kit of claim 1, wherein the embedding wells range from 15 to 50 mm in width, and range from 3 to 5 mm in depth.

8. The kit of claim 1, wherein an embedding well is notched.

9. The kit of claim 1, wherein the metallic chucks are made of stainless steel.

10. The kit of claim 1, wherein the metallic chucks are provided with a channeled face with a plurality of sharply cut channels that adhere to the embedding medium and allow extrusion of excess embedding medium.

11. The kit of claim 10, wherein the metallic chucks are provided with a stem disposed on a surface opposite of the channeled face.

12. The kit of claim 11, wherein the over-chuck cooling blocks are provided with a hole sized so that the cooling block can be placed over the stem of the chuck.

13. The kit of claim 10, wherein the metallic chucks comprise a means of attachment on a surface opposite of the channeled face, for use in cryostats requiring stemless or flat chucks.

14. The kit of claim 13, wherein the over-chuck cooling blocks comprise an indentation so that the cooling blocks can be placed over and attached to a stemless or flat metallic chuck.

15. The kit of claim 10, wherein the plurality of sharply cut channels form a grid.

16. The kit of claim 15, wherein the grid of channels is a rectangular grid.

17. The kit of claim 1, wherein the surfaces of the over-chuck cooling blocks are polished.

18. The kit of claim 1, wherein the over-chuck cooling blocks are made of stainless steel.

19. The kit of claim 1, further comprising
   a dislodging tool which when tapped on the metallic chuck or over chuck cooling block serves to free the frozen sample and metallic chuck from the well.

20. The kit of claim 19, wherein the dislodging tool is a cylindrical rod made of stainless steel.

21. The kit of claim 1, further comprising:
   a metallic freezing plate;
   an elevated metallic freezing block elevated by a plurality of footings, adapted to be placed on top of an embedded sample placed on the metallic freezing plate so as to form a frozen sample block; and
   a plastic cutting board for use in cutting the frozen sample block.

22. The kit of claim 21, wherein the metallic freezing plate is made of polished stainless steel.

23. The kit of claim 21, wherein the metallic freezing plate is part of the metallic platform.

24. The kit of claim 21, wherein the metallic freezing plate is part of a metallic bar separate from the metallic platform.

25. The kit of claim 21, wherein the cutting board is made of polyethylene.

26. The kit of claim 21, wherein the cutting board is attached to the metallic platform.

27. The kit of claim 21, wherein the cutting board is attached to a metallic bar separate from the metallic platform.

28. The kit of claim 21, wherein the plurality of footings of the elevated freezing block are from 3 to 5 mm long.

29. The kit of claim 21, wherein the elevated metallic freezing block has four footings.

30. The kit of claim 21, wherein the elevated metallic freezing block is made of stainless steel.

31. The kit of claim 21, wherein the system is adapted to be maintained at a temperature sufficiently cold for tissue samples to adhere to the metallic freezing plate.

32. The kit of claim 31, wherein the temperature is in the range of approximately −5 to −45 degrees centigrade.

33. The kit of claim 32, wherein the temperature is in the range of approximately −25 to −30 degrees centigrade.

34. The kit of claim 1, wherein the system is adapted to be maintained at a temperature sufficiently cold for tissue samples to adhere to the metallic platform.

35. The kit of claim 34, wherein the temperature is in the range of approximately −5 to −45 degrees centigrade.

36. The kit of claim 35, wherein the temperature is in the range of approximately −25 to −30 degrees centigrade.

37. The kit of claim 1, further comprising:
   a dispensing slide from which a wetted tissue can be accurately dispensed into a well;
   a tissue flattening tool used to flatten the wetted tissue sample on the embedding well floor as it is slid off the dispensing slide; and
   a prying tool for removing a frozen specimen from a well.

38. The kit of claim 37, wherein the dispensing slide is made of flexible plastic which narrows at one end.

39. The kit of claim 38, wherein the dispensing slide is about 1 mm thick, 25 mm wide narrowing to 15 mm wide at the narrow end.

40. The kit of claim 37, wherein the tissue flattening tool comprises a polished rounded bar that is the working end of a handle.

41. The kit of claim 40, wherein the rounded bar measures about 10 by 4 mm.

42. The kit of claim 40, wherein the handle of the tissue flattening tool is bent.

43. A method for preparing a tissue sample comprising the steps of:
  wetting a tissue sample with a drop of embedding medium;
  placing the tissue sample face down on the floor of a cooled embedding well;
  filling the embedding well with embedding medium to the brim of the well to create a meniscus of fluid above the level of the well;
  placing a chuck onto the protruding meniscus covering the well;
  placing an over-chuck cooling block over the chuck;
  freezing the sample for a period of time; and
  removing the sample and chuck from the embedding well.

44. The method of claim 43, wherein the period of time for freezing ranges from less than 20 seconds to one minute depending on the temperature of the apparatus and the volume of the well and tissue.

45. The method of claim 43, wherein the sample and chuck are removed from the embedding well by tapping the chuck or cooling block with a dislodging bar.

46. The method of claim 43, wherein the step of placing the tissue in the embedding well further comprises:
  placing the wetted sample at an end of a dispensing slide so that sample overhangs the end;
  placing the dispensing slide over the embedding well and pressing the overhanging sample to the well floor with a flattening tool;
  pulling the dispensing slide out from under the tissue; and
  flattening the tissue sample with the flattening tool as the sample is pulled off of the dispensing slide.

47. The method of claim 43, further comprising freezing the sample at a temperature sufficiently cold to adhere to the well floor.

48. The method of claim 47, wherein the temperature is in the range about −5 to about −45 degrees centigrade.

49. The method of claim 48, wherein the temperature is in the range about −25 to about −30 degrees centigrade.

50. The method of claim 43, further comprising warming the sample to an easy cutting temperature before cutting the sample.

* * * * *